US006881404B2

(12) United States Patent
Boodhoo et al.

(10) Patent No.: US 6,881,404 B2
(45) Date of Patent: Apr. 19, 2005

(54) HIGHLY PURIFIED MOCARHAGIN, A COBRA VENOM PROTEASE, POLYNUCLEOTIDES ENCODING SAME AND RELATED PROTEASES, AND THERAPEUTIC USES THEREOF

(75) Inventors: Amechand Boodhoo, Edmonton (CA); Jasbir S. Seehra, Lexington, MA (US); Gray Shaw, Cambridge, MA (US); Dianne Sako, Boston, MA (US)

(73) Assignee: Genetics Institute, LLC, Cambridge, MA (US)

( * ) Notice: Subject to any disclaimer, the term of this patent is extended or adjusted under 35 U.S.C. 154(b) by 258 days.

(21) Appl. No.: 09/996,620

(22) Filed: Nov. 27, 2001

(65) Prior Publication Data

US 2002/0127691 A1 Sep. 12, 2002

Related U.S. Application Data

(63) Continuation of application No. 09/026,001, filed on Feb. 18, 1998, now Pat. No. 6,413,760, which is a continuation-in-part of application No. 09/012,637, filed on Jan. 23, 1998, now abandoned, which is a continuation-in-part of application No. 08/843,373, filed on Apr. 15, 1997, now abandoned.

(51) Int. Cl.[7] .......................... A61K 38/48; C12N 9/64; C12N 15/57

(52) U.S. Cl. .................... 424/94.67; 435/226; 536/23.2
(58) Field of Search ........................ 435/226; 536/23.2; 424/94.67

(56) References Cited

U.S. PATENT DOCUMENTS 5,659,018 A    8/1997    Berndt et al. ............... 530/400

FOREIGN PATENT DOCUMENTS

WO    WO 97/05244 A1    2/1997

OTHER PUBLICATIONS

DeLuca, Mariagrazia et al., "A Novel Cobra Venom Metalloproteinase, Mocarhagin, Cleaves a 10–Amino Acid Peptide from the Mature N Terminus of P–selectin Glycoprotein Ligand Receptor, PSGL–1, and Abolishes P–selectin Binding." The Journal of Biological Chemistry Vo. 270, No. 45, Aug. 21, 1995, pp. 26734–26737.
Dong, Jing–fei et al., "Tyrosine Sulfation of the Glycoprotein Ib–IX Complex: Identification of Sulfated Residues and Effect on Ligand Binding." Biochemistry vol. 33, Aug. 31, 1994. pp. 13946–13953.
Kaufman, Randal J. et al., "Improved vectors for stable expression of foreign genes in mammalian cells by use of the untranslated leader sequence from EMC virus." Nucleic Acids Research vol. 19, No. 16, Jul. 22, 1991, pp. 4485–4490.

Kaufman, Randal J. et al., "Selection and Coamplification of Heterologous Genes in Mammalian Cells." Methods in Enzymology vol. 185, pp. 537–566. (1990).
Sako, Dianne et al. "Expression Cloning of a Functional Glycoprotein Ligand for P–Selectin." Cell, Dec. 17, 1993. vol. 75, pp. 1179–1186.
Spertini, Olivier et al., "P–selectin Glycoprotein Ligand 1 is a Ligand for L–Selectin on Neutrophils, Monocytes, and CD34+ Hematopoietic Progenitor Cells." Journal of Cell Biology vol. 135 No. 2, Oct. 1996. pp. 523–531.
Ward, Christopher M., et al., "Mocarhagin a Novel Cobra Venom Metaloproteinase, Cleaves the Platelet von \□illiebrand Factor Receptor Glycoprotein lbα. Identification of Sulfated Tyrosine/Anionic sequence yr–276–Glu–282 of Glycoprotein lbα as Binding Site for von Williebrand Factor and α–Thrombin." Biochemistry vol. 35, pp. 4929–4938 (1996).
Paine, Mark J. et al., "Cloning of metalloprotease genes in the carpet viper (*Echis pyramidum leakeyl*. Further members of the metalloprotease/disintegrin gene family" Eur. J. Biochem. 224, pp. 483–488 (1994).
Selistre de Arjuano, Heloisa S. et al., "Molecular Cloning and Sequence Analysis of cDNAs for Matalloproteinases from Broad–Banded Copperhead *Akistrodon contortrix laticinctus*." Archives of Biochemistry and Biophysics, vol. 320, No. 1, Jun. 20, 1995. pp. 141–148.
Zhou, Q. et al., "Molecular cloning and expression of catrocollastatin, a snake–venom protein from *Crotalus atrox* (western diamond rattlesnake) which inhibits platelet adhesion to collagen." Biochem. J., Apr. 15, 1995. 307 (Pt2); pp. 411–417.
Paine, Mark J.I., et al., Purification, Cloning, and Molecular Characterization of a High Molecular Weight Hemorrhagic Metalloprotease, Jararhagin, from *Bothrops jararaca* venom., Journal of Biological Chemistry, Nov. 15, 1992. vol. 267, No. 32, pp. 22869–22876.
Takeya, Hiroyuki, et al., "Primary Structure of $H_2$–Proteinase, a Non–Hemorrhagic Metalloproteinase, Isolated from the Venom of the Habu Snake, *Trimeresurus flavoviridis*." Biochem, J., vol. 106, No. 1, 1989. pp. 151–157.
Takeya, Hiroyuki, et al., "The Complete Amino Acid Sequence of the High Molecular Mass Hemorrhagic Protein HR1B Isolated from the Venom of *Trimeresurus flavoviridis*." Journal of Biological Chemistry, Sep. 25, 1990, vol. 265, No. 27, pp. 16068–16073.

(Continued)

*Primary Examiner*—Rebecca Prouty
(74) *Attorney, Agent, or Firm*—Finnegan, Henderson, Farabow, Garrett & Dunner, L.L.P.

(57) ABSTRACT

Highly purified mocarhagin, a cobra venom protease, is disclosed. Pharmaceutical compositions and therapeutic uses of the highly purified protease are also provided. Polynucleotides encoding such protease and related proteases are also disclosed.

45 Claims, 3 Drawing Sheets

OTHER PUBLICATIONS

Neeper, Michael P., et al., "Sequence of a cDNA encoding the platelet aggregation inhibitor trigramin." 1990 Oxford University Press, Nucleic Acids Research, vol. 18, No. 14, p. 4255.

Ogilvie, Mary Louise, et al., "Identification of Lectins in Snake Venoms." Journal of Herpetology, vol. 18, No. 3, pp. 285–290, 1984.

Gartner, T. Kent, et al., Isolation and characterization of three $Ca^{2+}$ dependent β–galactoside–specific lectins from snake venom. Biochem. J. (1984). vol. 224, 301–307.

Lo–Chun Au[1], et al., "A common precursor for a putative hemorrhagic protein and rhodostomin, a platelet aggregation inhibitor of the venom of *Calloselasma rhodostoma*: Molecular cloning and sequence analysis." Biochemical and Biophysical Research Communications. Dec. 16, 1991. vol. 181, No. 2, pp. 585–593.

Tan, Nget–Hong, et al., "A Comparative Study of Cobra (NAJA) Venom Enzymes." Compl. Biochem. Physiol., vol. 90B, No. 4, pp. 745–750, 1988.

Till, Gerd O., et al., "Intravascular Activation of Complement and Acute Lung Injury—Dependency on Neutrophils and Toxic Oxygen Metabolites." American Society for Clinical Investigation, Inc., May 1982, vol. 69, pp. 1126–1135.

Lefer, Allan M., Et Al., "Effects Of A Metalloproteinase That Truncates P–Selectin Glycoprotein Ligand On Neutrophil-Induced Cardiac Dysfunction in Ischemia/Reperfusion." J Mol ell Cardiol, vol. 30, 1998, pp. 002/007–007–007.

Albelda, Steven M., et al., "Adhesion molecules and inflammatory injury." The FASEB Journal, May, 1994, vol. 8, pp. 504–512.

Ward, P.A., et al., "Blocking of adhesion molecules in vivo as anti–inflammatory therapy." Therapeutic Immunology, 1994, vol. 1, pp. 165–171.

Fujimura, Y., et al., "Isolation and Characterization of Jararaca GPlb–BP, a Snake Venom Antagonist Specific to Platelet Glycoprotein lb." Thromb. Haemost, 1995, 74(2), pp. 743–750.

Takada, Moriatsu., et al., "The Cytokine–adhesion Molecule Cascade in Ischemia/Reperfusion Injury of the Rat Kidney." Amer. Soc. for Clinical Invest., Inc., Jun. 1997, vol. 99, pp. 2682–2690.

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 1:

```
Thr Asn Thr Pro Glu Gln Asp Arg Tyr Leu Gln Ala Lys Lys Tyr Ile
1               5                  10                 15

Glu Phe Tyr Val Val Val Asp Asn Val Met Tyr Arg Lys Tyr
            20                  25                 30
```

(2) INFORMATION FOR SEQ ID NO: 2:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 2:

```
Thr Asn Thr Pro Glu Gln Asp Arg Tyr Leu Gln Ala Lys Lys Tyr Ile
1               5                  10                 15

Glu Phe Tyr Val Val Val Asp Asn Val Met Tyr Arg Lys Tyr Thr Gly
            20                  25                 30

Lys Leu His Val Ile Thr Xaa Xaa Val Tyr Glu Met Asn Ala Leu Asn
            35                  40                 45
```

(2) INFORMATION FOR SEQ ID NO: 3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Glu Ala Thr Glu Tyr Glu Tyr Leu Asp Tyr Asp Phe Leu Pro Glu
1               5                  10                 15
```

(2) INFORMATION FOR SEQ ID NO: 4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO: 4:

```
Gln Ala Thr Glu Tyr Glu Tyr Leu Asp Tyr Asp Phe Leu Pro Glu
1               5                   10                  15
```

(2) INFORMATION FOR SEQ ID NO: 5:

(i) SEQUENCE CHARACTERISTICS:
        (A) LENGTH: 2050 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 78..1940

(xi) SEQUENCE DESCRIPTION: SEQ ID NO: 5:

```
AGTCAATAGG AGAAGAGCTC AGGTTGGCTT GGAAGCAGAA AGAGATTCCT GTCCACCACT      60
CCAATCCAGG CTCCAAAATG ATCCAAGCTC TCTTGGTAGC TATATGCTTA GCGGTTTTTC     120
CATATCAAGG GAGCTCTATA ATCCTGGAAT CCGGGAATGT TAATGATTAT GAAGTAGTGT     180
ATCCACAAAA AGTGCCTGCA TTGTCCAAAG GAGGAGTTCA GAATCCTCAG CCAGAGACCA     240
AGTATGAAGA TACAATGCAA TATGAATTTC ACGTGAACGG AGAGCCAGTG GTCCTTCACT     300
TAGAAAGAAA TAAAGGACTT TTTTCAGAAG ATTACACTGA AACTCATTAT GCCCCTGATG     360
GCAGAGAAAT TACAACAAGC TCTCCAGTTC AGGATCACTG CTATTATCAT GGTTACATTC     420
AGAATGAAGC TGACTCAAGT GCAGTCATCA GTGCATGTGA TGGCTTGAAA GGACATTTCA     480
AGCATCAAGG GGAGACATAC TTTATTGAGC CCTTGGAGCT TTCTGACAGT GAAGCCCATG     540
CAATATACAA AGATGAAAAT GTAGAAGAAG AGGAAGAGAT CCCCAAAATC TGTGGGGTTA     600
CCCAGACTAC TTGGGAATCA GATGAGCCGA TTGAAAAGTC CTCTCAGTTA ACTAATACTC     660
CTGAACAAGA CAGGTACTTG CAGGCCAAAA AATACATCGA GTTTTACGTG GTTGTGGACA     720
ATGTAATGTA CMGRAAATAC ACCGGCAAGT TACATGTTAT AACAAGAAGA GTATATGAAA     780
TGGTCAACGC TTTAAATACG ATGTACAGAC GTTTGAATTT TCACATAGCA CTGATTGGCC     840
TAGAAATTTG GTCCAACGGA AATGAGATTA ATGTGCAATC AGACGTGCAG GCCACTTTGG     900
ACTTATTTGG AGAATGGAGA GAAAATAAAT TGCTGCCACG CAAAAGGAAT GATAATGCTC     960
AGTTACTCAC GAGCACTGAG TTCAATGGAA CTACTACAGG ACTTGGTTAC ATAGGCTCCC    1020
TCTGTAGTCC GAAGAAATCT GTGGCAGTTG TTCAGGATCA TAGCAAAAGC ACAAGCATGG    1080
TGGCAATTAC AATGGCCCAT CAGATGGGTC ATAATCTGGG CATGAATGAT GACAGAGCTT    1140
CCTGTACTTG TGGTTCTAAC AAATGCATTA TGTCTACAAA ATATTATGAA TCTCTTTCTG    1200
AGTTCAGCTC TTGTAGTGTC CAGGAACATC GGGAGTATCT TCTTAGAGAC AGACCACAAT    1260
GCATTCTCAA CAAACCCTCG CGCAAAGCTA TTGTTACACC TCCAGTTTGT GGAAATTACT    1320
TTGTGGAGCG GGGAGAAGAA TGTGACTGTG GCTCTCCTGA GGATTGTCAA AATACCTGCT    1380
GTGATGCTGC AACTTGTAAA CTGCAACATG AGGCACAGTG TGACTCTGGA GAGTGTTGTG    1440
AGAAATGCAA ATTTAAGGGA GCAGGAGCAG AATGCCGGGC AGCAAAGAAT GACTGTGACT    1500
TTCCTGAACT CTGCACTGGC CGATCTGCTA AGTGTCCCAA GGACAGCTTC AGAGGAATGC    1560
GACATCCATG CCAAAACAAC CAAGGTTACT GCTACAATGG ACATGTCCC ACCTTGACAA    1620
ACCAATGTGC TACTCTCTGG GGGCCAGGTG CAAAAATGTC TCCAGGTTTA TGTTTTATGT    1680
TGAACTGGAA TGCCCGAAGT TGTGGCTTGT GCAGAAAGGA AAATGGCAGA AAGATTCTAT    1740
```

-continued

```
GTGCAGCAAA GGATGTAAAG TGTGGCAGGT TATTTTGCAA AAAGAAAAAC TCGATGATAT    1800

GCCACTGCCC ACTCCATCAA AGGACCCAAA TTATGGAATG GTTGCACCTG AACAAAATG     1860

TGGAGTTAAA AAGGTGTGCA GAAACAGGCA ATGTGTTAAA GTATAGACAG CCAACTGATC    1920

AAGCACTGCT TCTCTCAATT TGATTTTGGA GATCCTCCTT CCAGAAGGCT TTCCTCAAGT    1980

CCAAAGAGAC CCATCTGTCT TTATCCTACT AGTAAATCAC TCTTAGCTTT CAAAAAAAAA    2040

AAAAGTCGAC                                                          2050
```

(2) INFORMATION FOR SEQ ID NO: 6:

(i) SEQUENCE CHARACTERISTICS:
        (A) LENGTH: 621 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

```
Met Ile Gln Ala Leu Leu Val Ala Ile Cys Leu Ala Val Phe Pro Tyr
1               5                   10                  15

Gln Gly Ser Ser Ile Ile Leu Glu Ser Gly Asn Val Asn Asp Tyr Glu
            20                  25                  30

Val Val Tyr Pro Gln Lys Val Pro Ala Leu Ser Lys Gly Gly Val Gln
        35                  40                  45

Asn Pro Gln Pro Glu Thr Lys Tyr Glu Asp Thr Met Gln Tyr Glu Phe
    50                  55                  60

His Val Asn Gly Glu Pro Val Val Leu His Leu Glu Arg Asn Lys Gly
65                  70                  75                  80

Leu Phe Ser Glu Asp Tyr Thr Glu Thr His Tyr Ala Pro Asp Gly Arg
                85                  90                  95

Glu Ile Thr Thr Ser Ser Pro Val Gln Asp His Cys Tyr Tyr His Gly
            100                 105                 110

Tyr Ile Gln Asn Glu Ala Asp Ser Ser Ala Val Ile Ser Ala Cys Asp
        115                 120                 125

Gly Leu Lys Gly His Phe Lys His Gln Gly Glu Thr Tyr Phe Ile Glu
    130                 135                 140

Pro Leu Glu Leu Ser Asp Ser Glu Ala His Ala Ile Tyr Lys Asp Glu
145                 150                 155                 160

Asn Val Glu Glu Glu Glu Ile Pro Lys Ile Cys Gly Val Thr Gln
                165                 170                 175

Thr Thr Trp Glu Ser Asp Glu Pro Ile Glu Lys Ser Ser Gln Leu Thr
            180                 185                 190

Asn Thr Pro Glu Gln Asp Arg Tyr Leu Gln Ala Lys Lys Tyr Ile Glu
        195                 200                 205

Phe Tyr Val Val Asp Asn Val Met Tyr Arg Lys Tyr Thr Gly Lys
    210                 215                 220

Leu His Val Ile Thr Arg Arg Val Tyr Glu Met Val Asn Ala Leu Asn
225                 230                 235                 240

Thr Met Tyr Arg Arg Leu Asn Phe His Ile Ala Leu Ile Gly Leu Glu
                245                 250                 255

Ile Trp Ser Asn Gly Asn Glu Ile Asn Val Gln Ser Asp Val Gln Ala
            260                 265                 270

Thr Leu Asp Leu Phe Gly Glu Trp Arg Glu Asn Lys Leu Leu Pro Arg
        275                 280                 285
```

```
Lys Arg Asn Asp Asn Ala Gln Leu Leu Thr Ser Thr Glu Phe Asn Gly
290                 295                 300
Thr Thr Thr Gly Leu Gly Tyr Ile Gly Ser Leu Cys Ser Pro Lys Lys
305                 310                 315                 320
Ser Val Ala Val Val Gln Asp His Ser Lys Ser Thr Ser Met Val Ala
                325                 330                 335
Ile Thr Met Ala His Gln Met Gly His Asn Leu Gly Met Asn Asp Asp
            340                 345                 350
Arg Ala Ser Cys Thr Cys Gly Ser Asn Lys Cys Ile Met Ser Thr Lys
        355                 360                 365
Tyr Tyr Glu Ser Leu Ser Glu Phe Ser Ser Cys Ser Val Gln Glu His
    370                 375                 380
Arg Glu Tyr Leu Leu Arg Asp Arg Pro Gln Cys Ile Leu Asn Lys Pro
385                 390                 395                 400
Ser Arg Lys Ala Ile Val Thr Pro Pro Val Cys Gly Asn Tyr Phe Val
                405                 410                 415
Glu Arg Gly Glu Glu Cys Asp Cys Gly Ser Pro Glu Asp Cys Gln Asn
            420                 425                 430
Thr Cys Cys Asp Ala Ala Thr Cys Lys Leu Gln His Glu Ala Gln Cys
        435                 440                 445
Asp Ser Gly Glu Cys Cys Glu Lys Cys Lys Phe Lys Gly Ala Gly Ala
    450                 455                 460
Glu Cys Arg Ala Ala Lys Asn Asp Cys Asp Phe Pro Glu Leu Cys Thr
465                 470                 475                 480
Gly Arg Ser Ala Lys Cys Pro Lys Asp Ser Phe Gln Arg Asn Gly His
                485                 490                 495
Pro Cys Gln Asn Asn Gln Gly Tyr Cys Tyr Asn Gly Thr Cys Pro Thr
            500                 505                 510
Leu Thr Asn Gln Cys Ala Thr Leu Trp Gly Pro Gly Ala Lys Met Ser
        515                 520                 525
Pro Gly Leu Cys Phe Met Leu Asn Trp Asn Ala Arg Ser Cys Gly Leu
    530                 535                 540
Cys Arg Lys Glu Asn Gly Arg Lys Ile Leu Cys Ala Ala Lys Asp Val
545                 550                 555                 560
Lys Cys Gly Arg Leu Phe Cys Lys Lys Asn Ser Met Ile Cys His
                565                 570                 575
Cys Pro Leu His Gln Arg Thr Gln Ile Met Glu Trp Leu His Leu Glu
            580                 585                 590
Gln Asn Val Glu Leu Lys Arg Cys Ala Glu Thr Gly Asn Val Leu Lys
        595                 600                 605
Tyr Arg Gln Pro Thr Asp Gln Ala Leu Leu Leu Ser Ile
    610                 615                 620

(2) INFORMATION FOR SEQ ID NO: 7:

(i) SEQUENCE CHARACTERISTICS:
        (A) LENGTH: 2297 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

GTCGACCAGT CAACAGGAGA AAGCTCAGG TTGGCTTGGA AGCAGAAAGA GATTCCTGTC      60
```

```
CACCAGTCCA ATCCAGGCTC CAAAATGATC CAAGCTCTCT TGGTAATTAT ATGCTTAGCG      120
GTTTTTCCAT ATCAAGGGAG CTCTATAATC CTGGAATCTG GGAATGTTAA TGATTATGAA      180
GTTGTGTATC CACAAAAAGT GCCTGCATTG CTCAAAGGAG GAGTTCAGAA TCCTCAGCCA      240
GAGACCAAGT ATGAAGATAC AATGCAATAT GAATTTCAAG TGAATGGAGA GCCAGTAGTC      300
CTTCACTTAG AAAGAAATAA AGGACTTTTT TCAGAAGATT ACACTGAAAC TCATTATGCC      360
CCTGATGGCA GAGAAATTAC AACAAGCCCT CCGGTTCAGG ATCACTGCTA TTATCATGGT      420
TACATTCAGA ATGAAGCTGA CTCAAGTGCA ATCATCAGTG CATGTGATGG CTTGAAAGGA      480
CATTTCAAGC ATCAAGGGGA GACATACTTT ATTGAGCCCT TGAAGCTTTT CGACAGTGAA      540
TCTCATGCAA TCTACAAAGA TGAAAATGTA GAAAACGAGG ATGAGACCCC CGAAACCTGT      600
GGGGTAACCG AGACTACTTG GGAGTCAGAT GAGTCCATCG AAAAGACCTC TCAGTTAACT      660
AACACTCCTG AACAAGACGG GTACTTGCAG GCCAAAAAAT ACATCGAGTT TTACGTGGTT      720
GTGGACAACA GAATGTACAG GTATTACAAA CGCAATGAAC CTGCTATAAA AGAAGAGTA      780
TATGAAATGG TCAACGCTGT AAATACGAAG TACAGACCTT TGAAAATTCA CATAACACTG      840
ATTGGCCTAG AAATTTGGTC CAACCATGAT AAGTTTGAAG TGAAGCCAGT AGCGGGTGCC      900
ACTTTGAAAT CATTTCGAGA TTGGAGAGAA ACAGTTTTGC TGCCACGCAA AAGGAATGAT      960
AACGCTCAGT TACTCACGGG CATTGACTTC AATGGAACTG TTGTGGGAAT TGCTTACACG     1020
GGCACCCTCT GCACTCAGAA TTCTGTAGCA GTTGTTCAGG ATTATAACCG AAAAATAAGC     1080
ATGGTGGCAT CTACAATGGC CCATGAGTTG GGTCATAATC TGGGCCTTCA TCATGACGGA     1140
GCTTCCTGTA TTTGCAGTCT TAGACCATGC ATTATGTCTA AGGGACGGAC TGCACCTGCC     1200
TTTCAGTTCA GCTCTTGTAG TGTCCGGGAG TATCGGGAGT ATCTTCTTAG AGAAAGACCA     1260
CAATGCATTC TCAACAAACC CTTGAGCACA GATACTGTTT CACCTGCAAT TGTGGAAAT     1320
TACTTTGTGG AGGAGGGAGA AGAATGTGAC TGTGGCTCTC CTGCGGATTG TCAAAGTGCC     1380
TGCTGCGATG CTGCAACTTG TTAGTTTAAG GGAGAAGAAG CAGAATGCCG GGCAGCAAAG     1440
GATGACTGTG ACTTGCCTGA ACTCTGCACT GGCCGATCTG TGGAGTGTCC CACGGACAGC     1500
TTGCAGAAGA ATGGACATCC ATGTCAAAAC AACAAAGGTT ACTGCTACAA TGGGGCATGT     1560
CCCACCTTCA CAAACCAATG TATTGCTCTC ATGGGGACAG ATTTTACTGT GAGTCCAGAT     1620
GGATGTTTTG ACTTGAACGT GAGAGGGAAT GATGTAAGCC ACTGCAGAAA GGAAAATGGT     1680
GCAAAGATTC CATGTGCAGC AAAGGATGTA AAGTGTGGCA GGTTATACTG CACAGAGAGA     1740
GACACAATGT CATGCCGATT CCCACTGGAC CCAGATGGTG TAATGGCTGA ACCTGGAACA     1800
AAATGTGGAG ATGGAATGGT GTGCAGCAAC GGTCAGTGTG TTAATGTGCA GACAGCCTAC     1860
TGATCAAGCA CTGGCTTCTC TCAATTTGAT TTTGGAGATC CTCCTTCCAG AACGCTTCCC     1920
TCAAGTCCAA AGAGACCCAT CTGTCTTTAT CCTACTAGTA AATCACTCTT AGCTTTCAGA     1980
TGGTATCTAA AATTTATAAT ATTTCTTCTC CATAATTTAA ACTGGTAATC TTTTGCTAAA     2040
ATCAGACCTT TTCCCTGCCA CAAAGCTCCA TGGTCATGTA CAGCACCAAA GGCTTATTTG     2100
CGAATAAGAA AAAAAAATGG CAATTTTACA GTTTCCCAAT TGCAATGCAT ATTGAATGCA     2160
ACAAGCTCTG CCCTTTGAGC TGGCGTATTC AAAGGCAATG CTCCCTCTCC CAAAATTATA     2220
CGCTGGCTTT CCAAGATGTA GCTGCTTCCA TCAATAAACT ATTCTCATTC TGCAAAAAAA     2280
AAAAAAAAA AGTCGAC                                                    2297
```

(2) INFORMATION FOR SEQ ID NO: 8:

(i) SEQUENCE CHARACTERISTICS:
    (A) LENGTH: 439 amino acids
    (B) TYPE: amino acid
    (C) STRANDEDNESS: <Unknown>
    (D) TOPOLOGY: linear (ii) MOLECULE TYPE: protein (xi) SEQUENCE DESCRIPTION: SEQ ID NO: 8:

```
Met Ile Gln Ala Leu Leu Val Ile Ile Cys Leu Ala Val Phe Pro Tyr
1               5                   10                  15

Gln Gly Ser Ser Ile Ile Leu Glu Ser Gly Asn Val Asn Asp Tyr Glu
            20                  25                  30

Val Val Tyr Pro Gln Lys Val Pro Ala Leu Leu Lys Gly Gly Val Gln
        35                  40                  45

Asn Pro Gln Pro Glu Thr Lys Tyr Glu Asp Thr Met Gln Tyr Glu Phe
50                  55                  60

Gln Val Asn Gly Glu Pro Val Val Leu His Leu Glu Arg Asn Lys Gly
65                  70                  75                  80

Leu Phe Ser Glu Asp Tyr Thr Glu Thr His Tyr Ala Pro Asp Gly Arg
                85                  90                  95

Glu Ile Thr Thr Ser Pro Pro Val Gln Asp His Cys Tyr Tyr His Gly
            100                 105                 110

Tyr Ile Gln Asn Glu Ala Asp Ser Ser Ala Ile Ser Ala Cys Asp
        115                 120                 125

Gly Leu Lys Gly His Phe Lys His Gln Gly Glu Thr Tyr Phe Ile Glu
    130                 135                 140

Pro Leu Lys Leu Phe Asp Ser Glu Ser His Ala Ile Tyr Lys Asp Glu
145                 150                 155                 160

Asn Val Glu Asn Glu Asp Glu Thr Pro Glu Thr Cys Gly Val Thr Glu
                165                 170                 175

Thr Thr Trp Glu Ser Asp Glu Ser Ile Glu Lys Thr Ser Gln Leu Thr
            180                 185                 190

Asn Thr Pro Glu Gln Asp Gly Tyr Leu Gln Ala Lys Lys Tyr Ile Glu
        195                 200                 205

Phe Tyr Val Val Val Asp Asn Arg Met Tyr Arg Tyr Lys Arg Asn
    210                 215                 220

Glu Pro Ala Ile Lys Arg Arg Val Tyr Glu Met Val Asn Ala Val Asn
225                 230                 235                 240

Thr Lys Tyr Arg Pro Leu Lys Ile His Ile Thr Leu Ile Gly Leu Glu
                245                 250                 255

Ile Trp Ser Asn His Asp Lys Phe Glu Val Lys Pro Val Ala Gly Ala
            260                 265                 270

Thr Leu Lys Ser Phe Arg Asp Trp Arg Glu Thr Val Leu Leu Pro Arg
        275                 280                 285

Lys Arg Asn Asp Asn Ala Gln Leu Leu Thr Gly Ile Asp Phe Asn Gly
    290                 295                 300

Thr Val Val Gly Ile Ala Tyr Thr Gly Thr Leu Cys Thr Gln Asn Ser
305                 310                 315                 320

Val Ala Val Val Gln Asp Tyr Asn Arg Lys Ile Ser Met Val Ala Ser
                325                 330                 335

Thr Met Ala His Glu Leu Gly His Asn Leu Gly Leu His His Asp Gly
            340                 345                 350

Ala Ser Cys Ile Cys Ser Leu Arg Pro Cys Ile Met Ser Lys Gly Arg
        355                 360                 365
```

```
Thr Ala Pro Ala Phe Gln Phe Ser Ser Cys Ser Val Arg Glu Tyr Arg
    370                 375                 380

Glu Tyr Leu Leu Arg Glu Arg Pro Gln Cys Ile Leu Asn Lys Pro Leu
385                 390                 395                 400

Ser Thr Asp Thr Val Ser Pro Ala Ile Cys Gly Asn Tyr Phe Val Glu
                405                 410                 415

Glu Gly Glu Glu Cys Asp Cys Gly Ser Pro Ala Asp Cys Gln Ser Ala
            420                 425                 430

Cys Cys Asp Ala Ala Thr Cys
        435

(2) INFORMATION FOR SEQ ID NO: 9:

(i) SEQUENCE CHARACTERISTICS:
        (A) LENGTH: 2335 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

GTCGACCTCA GGTTGGCTTG AAGCAGAAA  GAGATTCCTA TCCACCACTC CAATCCAGGC      60

TCCAAAATGA TCCAAGCTCT CTTGGTAGCT ATATGCTTAG CGGTTTTTCC ATATCAAGGG     120

AGCTCTATAA TCCTGGAATC CGGGAATGTT AATGATTATG AAGTAGTGTA TCCACAAAAA     180

GTGCCTGCAT TGTCCAAAGG AGGAGTTCAG AATCCTCAGC CAGAGACCAA GTATGAAGAT     240

ACAATGCAAT ATGAATTTCA AGTGAATGGA GAGCCAGTAG TCCTTCACCT AGAAAGAAAT     300

AAAGGACTTT TTTCAGAAGA TTACACTGAA ACTCATTATG CCTCTGATGG CAGAGAAATT     360

ACAACAAGCC CACTCGTTCA GGATCACTGC TATTATCATG GTTACATTCA GAATGAAGCT     420

GACTCAAGTG CAGTCATCAG TGCATGCGAT GGCTTGAAAG ACATTTCGA  GCTTCAAGGG     480

GAGACATACT TTATTGAACC CTTGAAGATT TCCGACAGTG AAGCCCATGC AATCTACAAA     540

GATGAAAATG TAGAAAACGA GGATGAGACC CCCGAAACCT GTGGGGTAAC CGAGACTACT     600

TGGGAGTCAG ATGAGTCCAT TGAAAAGACC TCTCAGTTAA CTAACACTCC TGAACAAGAC     660

AGGTACTTGC AGGCCAAAAA ATACCTCGAG TTTTACGTGG TTGTGGACAA CATAATGTAC     720

AGGCATTACA AACGCGATAA ACCTGTTATA AAAAGAAGAG TATATGAAAT GATCAACACT     780

ATGAATATGG TGTACAATCG TTTGAATTTT CACATAGCAC TGATTGGCCT AGAAATTTGG     840

TCCAACAGAA ATGAGATTAA TGTGCAATCA GACGTGCAGG CCACTTTGGA CTTATTTGGA     900

GAATGGAGAG AAAAAAAATT GCTGCCACGC AAAAGGAATG ATAATGCTCA GTTACTCACG     960

GGTATTGACT TCAAAGGAAC TCCTGTAGGA CTTGCTTACA TAGGTTCCAT CTGCAATCCG    1020

AAGAGTTCTG TAGCAGTTGT TCAGGATTAT AGCAGTAGAA CAAGCATGGT GGCAATTACA    1080

ATGGCCCATG AGATGGGTCA TAATATGGGC ATTCATCATG ACGGACCTTC CTGTACTTGT    1140

GGTTCTAACA AATGCGTTAT GTCTACAAGA CGTACTGAAC CTGCCTATCA GTTCAGCTCT    1200

TGTAGTGTCC GGGAACATCA GGAGTATCTT CTTAGAGACA GACCACAATG CATTCTCAAC    1260

AAACCCTTGA GCACAGATAT TGTTTCACCT CCAATTTGTG GAAATAACTT GTGGAGGTG     1320

GGAGAAGAAT GTGACTGTGG CTCTCCTGCG GATTGTCAAA GTGCCTGCTG CGACGCTACA    1380

ACTTGTAAAC TACAACCTCA TGCACAGTGT GACTCCGAAG GGTGTTGTGA GAAATGCAAA    1440

TTTAAGGGAG CAGGAGCAGA ATGCCGGGCA GCAAAGGATG ACTGTGACTT GCCTGAACTC    1500

TGCACTGGCC AATCTGCTGA GTGTCCCACA GACATCTTCC AGAGGAATGG ACTTCCATGC    1560
```

-continued

```
CAAAACAACG AAGGTTACTG CTACAATGGG AAATGCCCCA TCATGACAAA CCAATGTATT    1620

GCTCTCCGGG GACCAGGTGT AAAAGTATCT CGAGATAGCT GTTTTACATT GAACCAGAGA    1680

ACCAGTGGTT GTGGCTTGTG CAGAATGGAA TATGGTAGAA AGATTCCATG TGCAGCAAAG    1740

GATGTAAAGT GTGGCAGGTT ATTTTGCAAA AAGGGAAACT CGATGATATG CAACTGCTCA    1800

GTTTCACCAC GTGACCCAAG TTATGGAATG GTTGAACCTG GAACAAAATG TGGAGATGGA    1860

ATGGTGTGCA GCAACAGGCA GTGTGTTGAT GTGAAGACAG CCTACTGATC AAGCACTGGC    1920

TTCTCTCAAT TTGATTTTGG AGGTCCTCCT TCCAGAACGC TTCCCTCAAG TCCAAAGAGA    1980

CCCATCTGTC TTTATCCTAC TAGTAAATCA CTCTTAGCTT TCAGATGGTA TCTAAAATTT    2040

AAAATATTTC TTCTCCATAA TTTAAACTGG TAATCTTTTG CTAAAATCAG ACCTTTTCCC    2100

TGCCACAAAG CTCCATGGTC ATGTACAGCA CCAAAGGCTT ATTTGCTAAC AAGAAAAAAA    2160

ATGGCCATTT TACTGTTTGC CAATTGCAAT TCACATTTAA TGCAACAAGC TCTGCCCTTT    2220

GAGCTGGCGT ACTCAAAGGC AATGCTCCCT CTCCCAAAAT TATACGCTGG CTTTCCAAGA    2280

TGTAGCTGCT TCCATCAATA AACTATTCTC ATTCTGAAAA AAAAAAAAAG TCGAC         2335
```

(2) INFORMATION FOR SEQ ID NO: 10:

(i) SEQUENCE CHARACTERISTICS:
        (A) LENGTH: 613 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 10:

```
Met Ile Gln Ala Leu Leu Val Ala Ile Cys Leu Ala Val Phe Pro Tyr
  1               5                  10                  15

Gln Gly Ser Ser Ile Ile Leu Glu Ser Gly Asn Val Asn Asp Tyr Glu
             20                  25                  30

Val Val Tyr Pro Gln Lys Val Pro Ala Leu Ser Lys Gly Gly Val Gln
         35                  40                  45

Asn Pro Gln Pro Glu Thr Lys Tyr Glu Asp Thr Met Gln Tyr Glu Phe
 50                  55                  60

Gln Val Asn Gly Glu Pro Val Val Leu His Leu Glu Arg Asn Lys Gly
 65                  70                  75                  80

Leu Phe Ser Glu Asp Tyr Thr Glu Thr His Tyr Ala Ser Asp Gly Arg
                 85                  90                  95

Glu Ile Thr Thr Ser Pro Leu Val Gln Asp His Cys Tyr Tyr His Gly
                100                 105                 110

Tyr Ile Gln Asn Glu Ala Asp Ser Ser Ala Val Ile Ser Ala Cys Asp
             115                 120                 125

Gly Leu Lys Gly His Phe Glu Leu Gln Gly Glu Thr Tyr Phe Ile Glu
         130                 135                 140

Pro Leu Lys Ile Ser Asp Ser Glu Ala His Ala Ile Tyr Lys Asp Glu
145                 150                 155                 160

Asn Val Glu Asn Glu Asp Glu Thr Pro Glu Thr Cys Gly Val Thr Glu
                165                 170                 175

Thr Thr Trp Glu Ser Asp Glu Ser Ile Glu Lys Thr Ser Gln Leu Thr
                180                 185                 190

Asn Thr Pro Glu Gln Asp Arg Tyr Leu Gln Ala Lys Lys Tyr Leu Glu
             195                 200                 205
```

```
Phe Tyr Val Val Asp Asn Ile Met Tyr Arg His Tyr Lys Arg Asp
    210                 215                 220
Lys Pro Val Ile Lys Arg Arg Val Tyr Glu Met Ile Asn Thr Met Asn
225                 230                 235                 240
Met Val Tyr Asn Arg Leu Asn Phe His Ile Ala Leu Ile Gly Leu Glu
                245                 250                 255
Ile Trp Ser Asn Arg Asn Glu Ile Asn Val Gln Ser Asp Val Gln Ala
            260                 265                 270
Thr Leu Asp Leu Phe Gly Glu Trp Arg Glu Lys Lys Leu Leu Pro Arg
        275                 280                 285
Lys Arg Asn Asp Asn Ala Gln Leu Leu Thr Gly Ile Asp Phe Lys Gly
290                 295                 300
Thr Pro Val Gly Leu Ala Tyr Ile Gly Ser Ile Cys Asn Pro Lys Ser
305                 310                 315                 320
Ser Val Ala Val Gln Asp Tyr Ser Ser Arg Thr Ser Met Val Ala
                325                 330                 335
Ile Thr Met Ala His Glu Met Gly His Asn Met Gly Ile His His Asp
                340                 345                 350
Gly Pro Ser Cys Thr Cys Gly Ser Asn Lys Cys Val Met Ser Thr Arg
                355                 360                 365
Arg Thr Glu Pro Ala Tyr Gln Phe Ser Ser Cys Ser Val Arg Glu His
    370                 375                 380
Gln Glu Tyr Leu Leu Arg Asp Arg Pro Gln Cys Ile Leu Asn Lys Pro
385                 390                 395                 400
Leu Ser Thr Asp Ile Val Ser Pro Pro Ile Cys Gly Asn Asn Phe Val
                405                 410                 415
Glu Val Gly Glu Glu Cys Asp Cys Gly Ser Pro Ala Asp Cys Gln Ser
                420                 425                 430
Ala Cys Cys Asp Ala Thr Thr Cys Lys Leu Gln Pro His Ala Gln Cys
        435                 440                 445
Asp Ser Glu Gly Cys Cys Glu Lys Cys Lys Phe Lys Gly Ala Gly Ala
    450                 455                 460
Glu Cys Arg Ala Ala Lys Asp Asp Cys Asp Leu Pro Glu Leu Cys Thr
465                 470                 475                 480
Gly Gln Ser Ala Glu Cys Pro Thr Asp Ile Phe Gln Arg Asn Gly Leu
                485                 490                 495
Pro Cys Gln Asn Asn Glu Gly Tyr Cys Tyr Asn Gly Lys Cys Pro Ile
                500                 505                 510
Met Thr Asn Gln Cys Ile Ala Leu Arg Gly Pro Gly Val Lys Val Ser
        515                 520                 525
Arg Asp Ser Cys Phe Thr Leu Asn Gln Arg Thr Ser Gly Cys Gly Leu
    530                 535                 540
Cys Arg Met Glu Tyr Gly Arg Lys Ile Pro Cys Ala Ala Lys Asp Val
545                 550                 555                 560
Lys Cys Gly Arg Leu Phe Cys Lys Lys Gly Asn Ser Met Ile Cys Asn
                565                 570                 575
Cys Ser Val Ser Pro Arg Asp Pro Ser Tyr Gly Met Val Glu Pro Gly
                580                 585                 590
Thr Lys Cys Gly Asp Gly Met Val Cys Ser Asn Arg Gln Cys Val Asp
        595                 600                 605
Val Lys Thr Ala Tyr
    610
```

(2) INFORMATION FOR SEQ ID NO: 11:

(i) SEQUENCE CHARACTERISTICS:
        (A) LENGTH: 2288 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 11:

```
AGTCAACAGG AGAAAAGCTC AGGTTGGCTT GGAAGCAGAA AGAGATTCCT GTCCACCAGT      60

CCAATCCAGG CTCCAAAATG ATCCAAGCTC TCTTGGTAAT TATATGCTTA GTGGTTTTTC     120

CATATCAAGG GAGCTCTATA ATCCTGGAAT CTGGGAATGT TAATGATTAT GAAGTTGTGT     180

ATCCACAAAA AGTGCCTGCA TTGCTCAAAG GAGGAGTTCA GAATCCTCAG CCAGAGACCA     240

AGTATGAAGA TACAATGCAA TATGAATTTC AAGTGAATGG AGAGCCAGTA GTCCTTCACT     300

TAGAAAGAAA TAAAGGACTT TTTTCAGAAG ATTACACTGA AACTCATTAT GCCCCTGATG     360

GCAGAGAAAT TACAACAAGC CCTCCGGTTC AGGATCACTG CTATTATCAT GGTTACATTC     420

AGAATGAAGC TGACTCAAGT GCAATCATCA GTGCATGTGA TGGCTTGAAA GGACATTTCA     480

AGCATCAAGG GGAGACATAC TTTATTGAGC CCTTGAAGCT TTTCGACAGT GAATCCCATG     540

CAATCTACAA AGATGAAAAT GTAGAAAACG AGGATGAGAC CCCCGAAACC TGTGGGGTAA     600

CCGAGACTAC TTGGGAGTCA GATGAGTCCA TCGAAAAGAC CTCTCAGTTA ACTAACACTC     660

CTGAACAAGA CGGGTACTTG CAGGCCAAAA AATACATCGA GTTTTACGTG GTTGTGGACA     720

ACAGAATGTA CAGGTATTAC AAACGCAATG AACCTGCTAT AAAAAGAAGA GTATATGAAA     780

TGGTCAACGC TGTAAATACG TACAGACCTT TGAAAATTCA CATAACACTG ATTGGCCTAG     840

AAATTTGGTC CAACGATGAT AAGTTTGAAG TGAAGCCAGT AGCGGGTGCC ACTTTGAAAT     900

CATTTCGAGA TTGGAGAGAA ACAGTTTTGC TGCCACGCAA AAGGAATGAT AACGCTCAGT     960

TACTCACGGG CATTGACTTC AATGGAACTG TTGTGGGAAT TGCTTACACG GGCACCCTCT    1020

GCACTCAGAA TTCTGTAGCA GTTGTTCAGG ATTATAACCG AAAAATAAGC ATGGTGGCAT    1080

CTACAATGGC CCATGAGTTG GGTCATAATC TGGGCCTTCA TCATGACGGA GCTTCCTGTA    1140

TTTGCAGTCT TAGACCATGC ATTATGTCTA AGGGACGGAC TGCACCTGCC TTTCAGTTCA    1200

GCTCTTGTAG TGTCCGGGAG TATCGGGAGT ATCTTCTTAG AGAAAGACCA CAATGCATTC    1260

TCAACAAACC CTTGAGCACA GATACTGTTT CACCTGCAAT TTGTGGAAAT TACTTTGTGG    1320

AGGAGGGAGA AGAATGTGAC TGTGGCTCTC CTGCGGATTG TCAAAGTGCC TGCTGCGATG    1380

CTGCAACTTG TAAGTTTAAG GGAGAAGAAG CAGAATGCCG GGCAGCAAAG GATGACTGTG    1440

ACTTGCCTGA ACTCTGCACT GGCCGATCTG TGGAGTGTCC CACGGACAGC TTGCAGGAGA    1500

ATGGACATCC ATGTCAAAAC AACAAAGGTT ACTGCTACAA TGGGGCATGT CCCACCTTCA    1560

CAAACCAATG TATTGCTCTC ATGGGACAG ATTTTACTGT GAGTCCAGAT GGATGTTTTG    1620

ACTTGAACGT GAGAGGGAAT TGATGTAAGC CACTGCAGAA AGGAAAATGG TGCAAAGATT    1680

CCATGTGCAG CAAAGGATGT AAAGTGTGGC AGATTATACT GCACAGAGAG AGACACAATG    1740

TCATGCCGAT TCCCACTGGA CCCAGATGGT GTTAATGGCT GAACCTGGAA CAAAATGTGG    1800

AGATGGAATG GTGTGCAGCA ACGGTCAGTG TGTTAATGTG CAGACAGCCT ACTGATCAAG    1860

CACTGGCTTC TCTCAATTTG ATTTTGGAGA TCCTCCTTCC AGAACGCTTC CCTCAAGTCC    1920

AAAGAGACCC ATCTGTCTTT ATCCTACTAG TAAATCACTC TTAGCTTTCA GATGGTATCT    1980

AAAATTTATA ATATTTCTTC TCCATAATTT AAACTGGTAA TCTTTTGCTA AAATCAGACC    2040
```

-continued

```
TTTTCCCTGC CACAAAGCTC CATGGTCATG TACAGCACCA AAGGCTTATT TGCGAATAAG    2100

AAAAAAAAAT GGCAATTTTA CAGTTTCCCA ATTGCAATGC ATATTGAATG CAACAAGCTC    2160

TGCCCTTTGA GCTGGCGTAT TCAAAGGCAA TGCTCCCTCT CCCAAAATTA TACGCTGGCT    2220

TTCCAAGATG TAGCTGCTTC CATCAATAAA CTATTCTCAT TCTGAAAAAA AAAAAAAAA     2280

AAGTCGAC                                                              2288
```

(2) INFORMATION FOR SEQ ID NO: 12:

(i) SEQUENCE CHARACTERISTICS:
        (A) LENGTH: 521 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 12:

```
Met Ile Gln Ala Leu Leu Val Ile Ile Cys Leu Val Val Phe Pro Tyr
1               5                   10                  15

Gln Gly Ser Ser Ile Ile Leu Glu Ser Gly Asn Val Asn Asp Tyr Glu
            20                  25                  30

Val Val Tyr Pro Gln Lys Val Pro Ala Leu Leu Lys Gly Gly Val Gln
        35                  40                  45

Asn Pro Gln Pro Glu Thr Lys Tyr Glu Asp Thr Met Gln Tyr Glu Phe
50                  55                  60

Gln Val Asn Gly Glu Pro Val Val Leu His Leu Glu Arg Asn Lys Gly
65                  70                  75                  80

Leu Phe Ser Glu Asp Tyr Thr Glu Thr His Tyr Ala Pro Asp Gly Arg
                85                  90                  95

Glu Ile Thr Thr Ser Pro Pro Val Gln Asp His Cys Tyr Tyr His Gly
            100                 105                 110

Tyr Ile Gln Asn Glu Ala Asp Ser Ser Ala Ile Ile Ser Ala Cys Asp
        115                 120                 125

Gly Leu Lys Gly His Phe Lys His Gln Gly Glu Thr Tyr Phe Ile Glu
    130                 135                 140

Pro Leu Lys Leu Phe Asp Ser Glu Ser His Ala Ile Tyr Lys Asp Glu
145                 150                 155                 160

Asn Val Glu Asn Glu Asp Glu Thr Pro Glu Thr Cys Gly Val Thr Glu
                165                 170                 175

Thr Thr Trp Glu Ser Asp Glu Ser Ile Glu Lys Thr Ser Gln Leu Thr
            180                 185                 190

Asn Thr Pro Glu Gln Asp Gly Tyr Leu Gln Ala Lys Lys Tyr Ile Glu
        195                 200                 205

Phe Tyr Val Val Asp Asn Arg Met Tyr Arg Tyr Lys Arg Asn
    210                 215                 220

Glu Pro Ala Ile Lys Arg Arg Val Tyr Glu Met Val Asn Ala Val Asn
225                 230                 235                 240

Thr Tyr Arg Pro Leu Lys Ile His Ile Thr Leu Ile Gly Leu Glu Ile
                245                 250                 255

Trp Ser Asn Asp Asp Lys Phe Glu Val Lys Pro Val Ala Gly Ala Thr
            260                 265                 270

Leu Lys Ser Phe Arg Asp Trp Arg Glu Thr Val Leu Leu Pro Arg Lys
        275                 280                 285

Arg Asn Asp Asn Ala Gln Leu Leu Thr Gly Ile Asp Phe Asn Gly Thr
```

```
              290             295             300
Val Val Gly Ile Ala Tyr Thr Gly Thr Leu Cys Thr Gln Asn Ser Val
305                 310                 315                 320

Ala Val Val Gln Asp Tyr Asn Arg Lys Ile Ser Met Val Ala Ser Thr
                325                 330                 335

Met Ala His Glu Leu Gly His Asn Leu Gly Leu His His Asp Gly Ala
            340                 345                 350

Ser Cys Ile Cys Ser Leu Arg Pro Cys Ile Met Ser Lys Gly Arg Thr
        355                 360                 365

Ala Pro Ala Phe Gln Phe Ser Ser Cys Ser Val Arg Glu Tyr Arg Glu
370                 375                 380

Tyr Leu Leu Arg Glu Arg Pro Gln Cys Ile Leu Asn Lys Pro Leu Ser
385                 390                 395                 400

Thr Asp Thr Val Ser Pro Ala Ile Cys Gly Asn Tyr Phe Val Glu Glu
                405                 410                 415

Gly Glu Glu Cys Asp Cys Gly Ser Pro Ala Asp Cys Gln Ser Ala Cys
                420                 425                 430

Cys Asp Ala Ala Thr Cys Lys Phe Lys Gly Glu Glu Ala Glu Cys Arg
                435                 440                 445

Ala Ala Lys Asp Asp Cys Asp Leu Pro Glu Leu Cys Thr Gly Arg Ser
450                 455                 460

Val Glu Cys Pro Thr Asp Ser Leu Gln Arg Asn Gly His Pro Cys Gln
465                 470                 475                 480

Asn Asn Lys Gly Tyr Cys Tyr Asn Gly Ala Cys Pro Thr Phe Thr Asn
                485                 490                 495

Gln Cys Ile Ala Leu Met Gly Thr Asp Phe Thr Val Ser Pro Asp Gly
            500                 505                 510

Cys Phe Asp Leu Asn Val Arg Gly Asn
        515                 520

(2) INFORMATION FOR SEQ ID NO: 13:

(i) SEQUENCE CHARACTERISTICS:
        (A) LENGTH: 2309 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 13:

GTCGACGTCA ACAGGAGAAA AGCTCAGGTT GGCTTGGAAG CAGAAAGAGA TTCCTGTCCA      60

CCAGTCCAAT CCAGGCTCCA AAATGATCCA AGCTCTCTTG GTAATTATAT GCTTAGTGGT     120

TTTTCCATAT CAAGGGAGCT CTATAATCCT GGAATCTGGG AATGTTAATG ATTATGAAGT     180

TGTGTATCCA CAAAAAGTGC CTGCATTGCT CAAAGGAGGA GTTCAGAATC CTCAGCCAGA     240

GACCAAGTAT GAAGATACAA TGCAATATGA ATTTCAAGTG AATGGAGAGC CAGTAGTCCT     300

TCACTTAGAA AGAAATAAAG GACTTTTTTC AGAAGATTAC ACTGAAACTC ATTATGCCCC     360

TGATGGCAGA GAAATTACAA CAAGCCCTCC GGTTCAGGAT CACTGCTATT ATCATGGTTA     420

CATTCAGAAT GAAGCTGACT CAAGTGCAAT CATCAGTGCA TGTGATGGCT TGAAAGGACA     480

TTTCAAGCAT CAAGGGGAGA CATACTTTAT TGAGCCCTTG AAGCTTTTCG ACAGTGAATC     540

CCATGCAATC TACAAAGATG AAAATGTAGA AACAGAGGAT GAGACCCCCG AAACCTGTGG     600

GGTAACCGAG ACTACTTGGG AGTCAGATGA GTCCATCGAA AAGACCTCTC AGTTAACTAA     660
```

```
CACTCCTGAA CAAGACGGGT ACTTGCAGGC CAAAAAATAC ATCGAGTTTT ACGTGGTTGT      720

GGACAACAGA ATGTACAGGT ATTACAAACG CAATGAACCT GCTATAAAAA GAAGAGTATA      780

TGAAATGGTC AACGCTGTAA ATACGAAGTA CAGACCTTTG AAAATTCACA TAACACTGAT      840

TGGCCTAGAA ATTTGGTCCA ACGATGATAA GTTTGAAGTG AAGCCAGTAG CGGGTGCCAC      900

TTTGAAATCA TTTCGAGATT GGAGAGAAAC AGTTTTGCTG CCACGCAAAA GGAATGATAA      960

CGCTCAGTTA CTCACGGGCA TTGACTTCAA TGGAACTGTT GTGGGAATTG CTTACACGGG     1020

CACCCTCTGC ACTCAGAATT CTGTAGCAGT TGTTCAGGAT TATAACCGAA AAATAAGCAT     1080

GGTGGCATCT ACAATGGCCC ATGAGTTGGG TCATAATCTG GCCTTCATC ATGACGGAGC      1140

TTCCTGTATT TGCAGTCTTA GACCATGCAT TATGTCTAAG GGACGGACTG CACCTGCCTT     1200

TCAGTTCAGC TCTTGTAGTG TCCGGGAGTA TCGGGAGTAT CTTCTTAGAG AAAGACCACA     1260

ATGCATTCTC AACAAACCCT TGAGCACAGA TACTGTTTCA CCTGCAATTT GTGGAAATTA     1320

CTTTGTGGAG GAGGGAGAAG AATGTGACTG TGGCTCTCCT GCGGATTGTC AAAGTGCCTG     1380

CTGCGATGCT GCAACTTGTA AGTTTAAGGG AGAAGAAGCA GAATGCCGGG CAGCAAAGGA     1440

TGACTGTGAC TTGCCTGAAC TCTGCACTGG CCGATCTGTG GAGTGTCCCA CGGACAGCTT     1500

GCAGAGGAAT GGACATCCAT GTCAAAACAA CAAAGGTTAC TGCTACAATG GGCATGTCC      1560

CACCTTCACA AACCAATGTA TTGCTCTCAT GGGGACAGAT TTTACTGTGA GTCCAGATGG     1620

ATGTTTTGAC TTGAACGTGA GAGGGAATGA TGTAAGCCAC TGCAGAAAGG AAAATGGTGC     1680

AAAGATTCCA TGTGCAGCAA AGGATGTAAA GTGTGGCAGG TTATACTGCA CAGAGAGAGA     1740

CACAATGTCA TGCCGATTCC CACTGGACCC AGATGGTGTA ATGGCTGAAC TGGAACAAA     1800

ATGTGGAGAT GGAATGGTGT GCAGCAACGG TCAGTGTGTT AATGTGCAGA CAGCCTACTG     1860

ATCAAGCACT GGCTTCTCTC AATTTGATTT TGGAGATCCT CCTTCCAGAA CGCTTCCCTC     1920

AAGTCCAAAG AGACCCATCT GTCTTTATCC TACTAGTAAA TCACTCTTAG CTTTCAGATG     1980

GTATCTAAAA TTTATAATAT TTCTTCTCCA TAATTTAAAC TGGTAATCTT TTGCTAAAAT     2040

CAGACCTTTT CCCTGCCACA AAGCTCCATG GTCATGTACA GCACCAAAGG CTTATTTGCG     2100

AATAAGAAAA AAAAATGGCA ATTTTACAGT TTCCCAATTG CAATGCATAT TGAATGCAAC     2160

AAGCTCTGCC CTTTGAGCTG GCGTATTCAA AGGCAATGCT CCCTCTCCCA AAATTATACG     2220

CTGGCTTTCC AAGATGTAGC TGCTTCCATC AATAAACTAT TCTCATTCTG AAAAAAAAA     2280

AAAAAAAAAA AAAAAAAAAA AAAGTCGAC                                     2309

(2) INFORMATION FOR SEQ ID NO: 14:

(i) SEQUENCE CHARACTERISTICS:
        (A) LENGTH: 592 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 14:

Met Ile Gln Ala Leu Leu Val Ile Ile Cys Leu Val Val Phe Pro Tyr
1               5                   10                  15

Gln Gly Ser Ser Ile Ile Leu Glu Ser Gly Asn Val Asn Asp Tyr Glu
            20                  25                  30

Val Val Tyr Pro Gln Lys Val Pro Ala Leu Leu Lys Gly Gly Val Gln
        35                  40                  45

Asn Pro Gln Pro Glu Thr Lys Tyr Glu Asp Thr Met Gln Tyr Glu Phe
```

-continued

```
                50                  55                  60
Gln Val Asn Gly Glu Pro Val Val Leu His Leu Glu Arg Asn Lys Gly
 65                  70                  75                  80

Leu Phe Ser Glu Asp Tyr Thr Glu Thr His Tyr Ala Pro Asp Gly Arg
                 85                  90                  95

Glu Ile Thr Thr Ser Pro Val Gln Asp His Cys Tyr Tyr His Gly
                100                 105                 110

Tyr Ile Gln Asn Glu Ala Asp Ser Ala Ile Ile Ser Ala Cys Asp
                115                 120                 125

Gly Leu Lys Gly His Phe Lys His Gln Gly Glu Thr Tyr Phe Ile Glu
130                 135                 140

Pro Leu Lys Leu Phe Asp Ser Glu Ser His Ala Ile Tyr Lys Asp Glu
145                 150                 155                 160

Asn Val Glu Asn Glu Asp Glu Thr Pro Glu Thr Cys Gly Val Thr Glu
                165                 170                 175

Thr Thr Trp Glu Ser Asp Glu Ser Ile Glu Lys Thr Ser Gln Leu Thr
                180                 185                 190

Asn Thr Pro Glu Gln Asp Gly Tyr Leu Gln Ala Lys Lys Tyr Ile Glu
                195                 200                 205

Phe Tyr Val Val Asp Asn Arg Met Tyr Arg Tyr Lys Arg Asn
210                 215                 220

Glu Pro Ala Ile Lys Arg Arg Val Tyr Glu Met Val Asn Ala Val Asn
225                 230                 235                 240

Thr Lys Tyr Arg Pro Leu Lys Ile His Ile Thr Leu Ile Gly Leu Glu
                245                 250                 255

Ile Trp Ser Asn Asp Asp Lys Phe Glu Val Lys Pro Val Ala Gly Ala
                260                 265                 270

Thr Leu Lys Ser Phe Arg Asp Trp Arg Glu Thr Val Leu Leu Pro Arg
                275                 280                 285

Lys Arg Asn Asp Asn Ala Gln Leu Leu Thr Gly Ile Asp Phe Asn Gly
290                 295                 300

Thr Val Val Gly Ile Ala Tyr Thr Gly Thr Leu Cys Thr Gln Asn Ser
305                 310                 315                 320

Val Ala Val Val Gln Asp Tyr Asn Arg Lys Ile Ser Met Val Ala Ser
                325                 330                 335

Thr Met Ala His Glu Leu Gly His Asn Leu Gly Leu His His Asp Gly
                340                 345                 350

Ala Ser Cys Ile Cys Ser Leu Arg Pro Cys Ile Met Ser Lys Gly Arg
                355                 360                 365

Thr Ala Pro Ala Phe Gln Phe Ser Ser Cys Ser Val Arg Glu Tyr Arg
                370                 375                 380

Glu Tyr Leu Leu Arg Glu Arg Pro Gln Cys Ile Leu Asn Lys Pro Leu
385                 390                 395                 400

Ser Thr Asp Thr Val Ser Pro Ala Ile Cys Gly Asn Tyr Phe Val Glu
                405                 410                 415

Glu Gly Glu Glu Cys Asp Cys Gly Ser Pro Ala Asp Cys Gln Ser Ala
                420                 425                 430

Cys Cys Asp Ala Ala Thr Cys Lys Phe Lys Gly Glu Glu Ala Glu Cys
                435                 440                 445

Arg Ala Ala Lys Asp Asp Cys Asp Leu Pro Glu Leu Cys Thr Gly Arg
                450                 455                 460

Ser Val Glu Cys Pro Thr Asp Ser Leu Gln Arg Asn Gly His Pro Cys
465                 470                 475                 480
```

```
Gln Asn Asn Lys Gly Tyr Cys Tyr Asn Gly Ala Cys Pro Thr Phe Thr
            485                 490                 495
Asn Gln Cys Ile Ala Leu Met Gly Thr Asp Phe Thr Val Ser Pro Asp
        500                 505                 510
Gly Cys Phe Asp Leu Asn Val Arg Gly Asn Asp Val Ser His Cys Arg
            515                 520                 525
Lys Glu Asn Gly Ala Lys Ile Pro Cys Ala Ala Lys Asp Val Lys Cys
        530                 535                 540
Gly Arg Leu Tyr Cys Thr Glu Arg Asp Thr Met Ser Cys Arg Phe Pro
545                 550                 555                 560
Leu Asp Pro Asp Gly Val Met Ala Glu Pro Gly Thr Lys Cys Gly Asp
            565                 570                 575
Gly Met Val Cys Ser Asn Gly Gln Cys Val Asn Val Gln Thr Ala Tyr
            580                 585                 590

(2) INFORMATION FOR SEQ ID NO: 15:

(i) SEQUENCE CHARACTERISTICS:
        (A) LENGTH: 1820 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 15:
```

| | |
|---|---:|
| GTCGACGACA TTTCAAGCAT CAAGGGGAGA CATACTTTAT TGAGCCCTTG AAGCTTTTCG | 60 |
| ACAGTGAATC CCATGCAATC TACAAAGATG AAAATGTAGA AAACGAGGAT GAGACCCCCG | 120 |
| AAACCTGTGG GGTAACCGAG ACTACTTGGG AGTCAGATGA GTCCATTGAA AAGACCTCTC | 180 |
| AGTTAACTAA CACTCCTGAA CAAGACGGGT ACTTGCAGGC CAAAAAATAC ATCGAGTTTT | 240 |
| ACGTGGTTGT GGACAACAGA ATGTACAGGT ATTACAAACG CAATGAACCT GCTATAAAAA | 300 |
| GAAGAGTATA TGAAATGGTC AACGCTGTAA ATACGAAGTA CAGACCTTTG AAAATTCACA | 360 |
| TAAACACTGAT TGGCCTAGAA ATTTGGTCCA ACGATGATAA GTTTGAAGTG AAGCCAGTAG | 420 |
| CGGGTGCCAC TTTGAAATCA TTTCGAGATT GGAGAGAAAC AGTTTTGCTG CCACGCAAAA | 480 |
| GGAATGATAA CGCTCAGTTA CTCACGGGCA TTGACTTCAA TGGAACTGTT GTGGGAATTG | 540 |
| CTTACACGGG CACCCTCTGC ACTCAGAATT CTGTAGCAGT TGTTCAGGAT TATAACCGAA | 600 |
| AAATAAGCAT GGTGGCATCT ACAATGGCCC ATGAGTTGGG TCATAATCTG GCATTCATC | 660 |
| ATGACGGAGC TTCCTGTATT TGCAGTCTTA AACCATGCAT TATGTCTAAG GGACGGACTG | 720 |
| CACCTGCCTT TCAGTTCAGC TCTTGTAGTG TCCGGGAGTA TCGGGAGTAT CTTCTTAGAA | 780 |
| AAAGACCACA ATGCATTCTC AACAAACCCT TGAGCACAGA TATTGTTTCA CCTGCAATTT | 840 |
| GTGGAAATTA CTTTGTGGAG GAGGGAGAAG AATGTGACTG TGGCTCTCCT GCGGATTGTC | 900 |
| AAAGTGCCTG CTGCAATGCT GCAACTTGTA AGTTTAAGGG AGAAGAAGCA GAATGCCGGG | 960 |
| CAGCAAAGGA TGACTGTGAC TTGCCTGAAC TCTGCACTGG CCGATCTGTG GAGTGTCCCA | 1020 |
| CGGACAGCTT GCAGAGGAAT GGACATCCAT GTCAAAACAA CAAGGTTAC TGCTACAATG | 1080 |
| GGGCATGTCC CACCTTCACA AACCAATGTA TTGCTCTCAT GGGACAGAT TTTACTGTGA | 1140 |
| GTCCAGATGG ATGTTTTGAC TTGAACGTGA GAGGGAATGA TGTAAGCCAC TGCAGAAAGG | 1200 |
| AAAATGGTGC AAAGATTCCA TGTGCAGCAA AGGATGTAAA GTGTGGCAGG TTATACTGCA | 1260 |
| CAGAGAGAAA CACAATGTCA TGCCGATTCC CACTGGACCC AGATGGTGTA ATGGCTGAAC | 1320 |

-continued

```
CTGGAACAAA ATGTGGAGAT GGAATGGTGT GCAGCAACGG TCAGTGTGTT AATGTGCAGA      1380

CAGCCTACTG ATCAAGCACT GGCTTCTCTC AATTTGATTT TGGAGATCCT CCTTCCAGAA      1440

CGCTTCCCTC AAGTCCAAAG AGACCCATCT GTCTTTATCC TACTAGTAAA TCACTCTTAG      1500

CTTTCAGATG GTATCTAAAA TTTATAATAT TTCTTCTCCA TAATTTAAAC TGGTAATCTT      1560

TTGCTAAAAT CAGACCTTTT CCCTGCCACA AAGCTCCATG GTCATGTACA GTACCAAAGG      1620

CTTATTTGCT AACACGAAAA AAAATGGCCA TTTTACCGTT TGCCAATTGC AATTCACATT      1680

TAATGCAACA AGCTCTGCCC TTTGAGCTGG CGTATTCAAA GGCAATGCTC CCTCTCCCAA      1740

AATTATATGC TGGCTTTCCA AGATGTAGCT GCTTCCATCA ATAAACTATT CTCATTCTGA      1800

AAAAAAAAAA AAAAGTCGAC                                                  1820
```

(2) INFORMATION FOR SEQ ID NO: 16:

(i) SEQUENCE CHARACTERISTICS:
        (A) LENGTH: 462 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 16:

```
Arg Arg His Phe Lys His Gln Gly Glu Thr Tyr Phe Ile Glu Pro Leu
 1               5                  10                  15

Lys Leu Phe Asp Ser Glu Ser His Ala Ile Tyr Lys Asp Glu Asn Val
            20                  25                  30

Glu Asn Glu Asp Glu Thr Pro Glu Thr Cys Gly Val Thr Glu Thr Thr
        35                  40                  45

Trp Glu Ser Asp Glu Ser Ile Glu Lys Thr Ser Gln Leu Thr Asn Thr
    50                  55                  60

Pro Glu Gln Asp Gly Tyr Leu Gln Ala Lys Lys Tyr Ile Glu Phe Tyr
65                  70                  75                  80

Val Val Val Asp Asn Arg Met Tyr Arg Tyr Lys Arg Asn Glu Pro
                85                  90                  95

Ala Ile Lys Arg Arg Val Tyr Glu Met Val Asn Ala Val Asn Thr Lys
            100                 105                 110

Tyr Arg Pro Leu Lys Ile His Ile Thr Leu Ile Gly Leu Glu Ile Trp
        115                 120                 125

Ser Asn Asp Asp Lys Phe Glu Val Lys Pro Val Ala Gly Ala Thr Leu
    130                 135                 140

Lys Ser Phe Arg Asp Trp Arg Glu Thr Val Leu Leu Pro Arg Lys Arg
145                 150                 155                 160

Asn Asp Asn Ala Gln Leu Leu Thr Gly Ile Asp Phe Asn Gly Thr Val
                165                 170                 175

Val Gly Ile Ala Tyr Thr Gly Thr Leu Cys Thr Gln Asn Ser Val Ala
            180                 185                 190

Val Val Gln Asp Tyr Asn Arg Lys Ile Ser Met Val Ala Ser Thr Met
        195                 200                 205

Ala His Glu Leu Gly His Asn Leu Gly Ile His His Asp Gly Ala Ser
    210                 215                 220

Cys Ile Cys Ser Leu Lys Pro Cys Ile Met Ser Lys Gly Arg Thr Ala
225                 230                 235                 240

Pro Ala Phe Gln Phe Ser Ser Cys Ser Val Arg Glu Tyr Arg Glu Tyr
                245                 250                 255
```

```
Leu Leu Arg Lys Arg Pro Gln Cys Ile Leu Asn Lys Pro Leu Ser Thr
            260                 265                 270

Asp Ile Val Ser Pro Ala Ile Cys Gly Asn Tyr Phe Val Glu Glu Gly
            275                 280                 285

Glu Glu Cys Asp Cys Gly Ser Pro Ala Asp Cys Gln Ser Ala Cys Cys
            290                 295                 300

Asn Ala Ala Thr Cys Lys Phe Lys Gly Glu Glu Ala Glu Cys Arg Ala
305                 310                 315                 320

Ala Lys Asp Asp Cys Asp Leu Pro Glu Leu Cys Thr Gly Arg Ser Val
                325                 330                 335

Glu Cys Pro Thr Asp Ser Leu Gln Arg Asn Gly His Pro Cys Gln Asn
            340                 345                 350

Asn Lys Gly Tyr Cys Tyr Asn Gly Ala Cys Pro Thr Phe Thr Asn Gln
            355                 360                 365

Cys Ile Ala Leu Met Gly Thr Asp Phe Thr Val Ser Pro Asp Gly Cys
370                 375                 380

Phe Asp Leu Asn Val Arg Gly Asn Asp Val Ser His Cys Arg Lys Glu
385                 390                 395                 400

Asn Gly Ala Lys Ile Pro Cys Ala Ala Lys Asp Val Lys Cys Gly Arg
                405                 410                 415

Leu Tyr Cys Thr Glu Arg Asn Thr Met Ser Cys Arg Phe Pro Leu Asp
            420                 425                 430

Pro Asp Gly Val Met Ala Glu Pro Gly Thr Lys Cys Gly Asp Gly Met
            435                 440                 445

Val Cys Ser Asn Gly Gln Cys Val Asn Val Gln Thr Ala Tyr
450                 455                 460

(2) INFORMATION FOR SEQ ID NO: 17:

(i) SEQUENCE CHARACTERISTICS:
        (A) LENGTH: 2359 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 17:

GTCGACCTCA GGTTGGCTTG GAAGCAGAAA GAGATTCCTA TCCACCACTC CAATCCAGGC      60

TCCAAAATGA TCCAAGCTCT CTTGGTAGCT ATATGCTTAG CGGTTTTTCC ATATCAAGGG     120

AGCTCTATAA TCCTGGAATC CGGGAATGTT AATGATTATG AAGTAGTGTA TCCACAAAAA     180

GTGCCTGCAT TGTCCAAAGG AGGAGTTCAG AATCCTCAGC CAGAGACCAA GTATGAAGAT     240

ACAATGCAAT ATGAATTTCA AGTGAATGGA GAGCCAGTAG TCCTTCACCT AGAAAGAAAT     300

AAAGGACTTT TTTCAGAAGA TTACACTGAA ACTCATTATG CCTCTGATGG CAGAGAAATT     360

ACAACAAGCC CACTCGTTCA GGATCACTGC TATTATCATG GTTACATTCA GAATGAAGCT     420

GACTCAAGTG CAGTCATCAG TGCATGCGAT GGCTTGAAAG ACATTTCGA GCTTCAAGGG     480

GAGACATACT TTATTGAACC CTTGAAGATT TCCGACAGTG AAGCCCATGC AATCTACAAA     540

GATGAAAATG TAGAAAACGA GGATGAGACC CCCGAAACCT GTGGGGTAAC CGAGACTACT     600

TGGGAGTCAG ATGAGTCCAT TGAAAAGACC TCTCAGTTAG ACGACGACGA CAAGCGGCCG     660

CCAACTAACA CTCCTGAACA AGACAGGTAC TTGCAGGCCA AAAATACCT CGAGTTTTAC     720

GTGGTTGTGG ACAACATAAT GTACAGGCAT TACAAACGCG ATAAACCTGT TATAAAAGA     780

AGAGTATATG AAATGATCAA CACTATGAAT ATGGTGTACA ATCGTTTGAA TTTTCACATA     840
```

```
GCACTGATTG GCCTAGAAAT TTGGTCCAAC AGAAATGAGA TTAATGTGCA ATCAGACGTG    900

CAGGCCACTT TGGACTTATT TGGAGAATGG AGAGAAAAAA AATTGCTGCC ACGCAAAAGG    960

AATGATAATG CTCAGTTACT CACGGGTATT GACTTCAAAG GAACTCCTGT AGGACTTGCT   1020

TACATAGGTT CCATCTGCAA TCCGAAGAGT TCTGTAGCAG TTGTTCAGGA TTATAGCAGT   1080

AGAACAAGCA TGGTGGCAAT TACAATGGCC CATGAGATGG GTCATAATAT GGGCATTCAT   1140

CATGACGGAC CTTCCTGTAC TTGTGGTTCT AACAAATGCG TTATGTCTAC AAGACGTACT   1200

GAACCTGCCT ATCAGTTCAG CTCTTGTAGT GTCCGGGAAC ATCAGGAGTA TCTTCTTAGA   1260

GACAGACCAC AATGCATTCT CAACAAACCC TTGAGCACAG ATATTGTTTC ACCTCCAATT   1320

TGTGGAAATA ACTTTGTGGA GGTGGGAGAA GAATGTGACT GTGGCTCTCC TGCGGATTGT   1380

CAAAGTGCCT GCTGCGACGC TACAACTTGT AAACTACAAC CTCATGCACA GTGTGACTCC   1440

GAAGGGTGTT GTGAGAAATG CAAATTTAAG GGAGCAGGAG CAGAATGCCG GGCAGCAAAG   1500

GATGACTGTG ACTTGCCTGA ACTCTGCACT GGCCAATCTG CTGAGTGTCC CACAGACATC   1560

TTCCAGAGGA ATGGACTTCC ATGCCAAAAC AACGAAGGTT ACTGCTACAA TGGGAAATGC   1620

CCCATCATGA CAAACCAATG TATTGCTCTC CGGGGACCAG GTGTAAAAGT ATCTCGAGAT   1680

AGCTGTTTTA CATTGAACCA GAGAACCAGT GGTTGTGGCT TGTGCAGAAT GGAATATGGT   1740

AGAAAGATTC CATGTGCAGC AAAGGATGTA AAGTGTGGCA GGTTATTTTG CAAAAAGGGA   1800

AACTCGATGA TATGCAACTG CTCAGTTTCA CCACGTGACC CAAGTTATGG AATGGTTGAA   1860

CCTGGAACAA AATGTGGAGA TGGAATGGTG TGCAGCAACA GGCAGTGTGT TGATGTGAAG   1920

ACAGCCTACT GATCAAGCAC TGGCTTCTCT CAATTTGATT TTGGAGGTCC TCCTTCCAGA   1980

ACGCTTCCCT CAAGTCCAAA GAGACCCATC TGTCTTTATC CTACTAGTAA ATCACTCTTA   2040

GCTTTCAGAT GGTATCTAAA ATTTAAAATA TTTCTTCTCC ATAATTTAAA CTGGTAATCT   2100

TTTGCTAAAA TCAGACCTTT TCCCTGCCAC AAAGCTCCAT GGTCATGTAC AGCACCAAAG   2160

GCTTATTTGC TAACAAGAAA AAAAATGGCC ATTTTACTGT TTGCCAATTG CAATTCACAT   2220

TTAATGCAAC AAGCTCTGCC CTTTGAGCTG GCGTACTCAA AGGCAATGCT CCCTCTCCCA   2280

AAATTATACG CTGGCTTTCC AAGATGTAGC TGCTTCCATC AATAAACTAT TCTCATTCTG   2340

AAAAAAAAAA AAAGTCGAC                                                2359

(2) INFORMATION FOR SEQ ID NO: 18:

(i) SEQUENCE CHARACTERISTICS:
         (A) LENGTH: 621 amino acids
         (B) TYPE: amino acid
         (C) STRANDEDNESS: <Unknown>
         (D) TOPOLOGY: linear (ii) MOLECULE TYPE: protein (xi) SEQUENCE DESCRIPTION: SEQ ID NO: 18:

Met Ile Gln Ala Leu Leu Val Ala Ile Cys Leu Ala Val Phe Pro Tyr
1               5                   10                  15

Gln Gly Ser Ser Ile Ile Leu Glu Ser Gly Asn Val Asn Asp Tyr Glu
            20                  25                  30

Val Val Tyr Pro Gln Lys Val Pro Ala Leu Ser Lys Gly Gly Val Gln
        35                  40                  45

Asn Pro Gln Pro Glu Thr Lys Tyr Glu Asp Thr Met Gln Tyr Glu Phe
    50                  55                  60

Gln Val Asn Gly Glu Pro Val Val Leu His Leu Glu Arg Asn Lys Gly
```

-continued

```
                65                  70                  75                  80
Leu Phe Ser Glu Asp Tyr Thr Glu Thr His Tyr Ala Ser Asp Gly Arg
                    85                  90                  95
Glu Ile Thr Thr Ser Pro Leu Val Gln Asp His Cys Tyr Tyr His Gly
                    100                 105                 110
Tyr Ile Gln Asn Glu Ala Asp Ser Ser Ala Val Ile Ser Ala Cys Asp
                    115                 120                 125
Gly Leu Lys Gly His Phe Glu Leu Gln Gly Glu Thr Tyr Phe Ile Glu
        130                 135                 140
Pro Leu Lys Ile Ser Asp Ser Glu Ala His Ala Ile Tyr Lys Asp Glu
145                 150                 155                 160
Asn Val Glu Asn Glu Asp Glu Thr Pro Glu Thr Cys Gly Val Thr Glu
                    165                 170                 175
Thr Thr Trp Glu Ser Asp Glu Ser Ile Glu Lys Thr Ser Gln Leu Asp
                    180                 185                 190
Asp Asp Asp Lys Arg Pro Pro Thr Asn Thr Pro Glu Gln Asp Arg Tyr
                    195                 200                 205
Leu Gln Ala Lys Lys Tyr Leu Glu Phe Tyr Val Val Val Asp Asn Ile
        210                 215                 220
Met Tyr Arg His Tyr Lys Arg Asp Lys Pro Val Ile Lys Arg Arg Val
225                 230                 235                 240
Tyr Glu Met Ile Asn Thr Met Asn Met Val Tyr Asn Arg Leu Asn Phe
                    245                 250                 255
His Ile Ala Leu Ile Gly Leu Glu Ile Trp Ser Asn Arg Asn Glu Ile
                    260                 265                 270
Asn Val Gln Ser Asp Val Gln Ala Thr Leu Asp Leu Phe Gly Glu Trp
                    275                 280                 285
Arg Glu Lys Lys Leu Leu Pro Arg Lys Arg Asn Asp Asn Ala Gln Leu
        290                 295                 300
Leu Thr Gly Ile Asp Phe Lys Gly Thr Pro Val Gly Leu Ala Tyr Ile
305                 310                 315                 320
Gly Ser Ile Cys Asn Pro Lys Ser Ser Val Ala Val Val Gln Asp Tyr
                    325                 330                 335
Ser Ser Arg Thr Ser Met Val Ala Ile Thr Met Ala His Glu Met Gly
                    340                 345                 350
His Asn Met Gly Ile His His Asp Gly Pro Ser Cys Thr Cys Gly Ser
                    355                 360                 365
Asn Lys Cys Val Met Ser Thr Arg Arg Thr Glu Pro Ala Tyr Gln Phe
        370                 375                 380
Ser Ser Cys Ser Val Arg Glu His Gln Glu Tyr Leu Leu Arg Asp Arg
385                 390                 395                 400
Pro Gln Cys Ile Leu Asn Lys Pro Leu Ser Thr Asp Ile Val Ser Pro
                    405                 410                 415
Pro Ile Cys Gly Asn Asn Phe Val Glu Val Gly Glu Glu Cys Asp Cys
                    420                 425                 430
Gly Ser Pro Ala Asp Cys Gln Ser Ala Cys Cys Asp Ala Thr Thr Cys
        435                 440                 445
Lys Leu Gln Pro His Ala Gln Cys Asp Ser Glu Gly Cys Cys Glu Lys
        450                 455                 460
Cys Lys Phe Lys Gly Ala Gly Ala Glu Cys Arg Ala Ala Lys Asp Asp
465                 470                 475                 480
Cys Asp Leu Pro Glu Leu Cys Thr Gly Gln Ser Ala Glu Cys Pro Thr
                    485                 490                 495
```

```
Asp Ile Phe Gln Arg Asn Gly Leu Pro Cys Gln Asn Asn Glu Gly Tyr
            500                 505                 510
Cys Tyr Asn Gly Lys Cys Pro Ile Met Thr Asn Gln Cys Ile Ala Leu
            515                 520                 525
Arg Gly Pro Gly Val Lys Val Ser Arg Asp Ser Cys Phe Thr Leu Asn
            530                 535                 540
Gln Arg Thr Ser Gly Cys Gly Leu Cys Arg Met Glu Tyr Gly Arg Lys
545                 550                 555                 560
Ile Pro Cys Ala Ala Lys Asp Val Lys Cys Gly Arg Leu Phe Cys Lys
            565                 570                 575
Lys Gly Asn Ser Met Ile Cys Asn Cys Ser Val Ser Pro Arg Asp Pro
            580                 585                 590
Ser Tyr Gly Met Val Glu Pro Gly Thr Lys Cys Gly Asp Gly Met Val
            595                 600                 605
Cys Ser Asn Arg Gln Cys Val Asp Val Lys Thr Ala Tyr
            610                 615                 620
```

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 19:

ACNCCNGARC ARGAY                                                      15

(2) INFORMATION FOR SEQ ID NO: 20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 20:

RTAYTTYCKR TACAT                                                      15

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 21:

CAGGACAGGT ACTTGCAGGC CAAA                                    24

(2) INFORMATION FOR SEQ ID NO: 22:

(i) SEQUENCE CHARACTERISTICS:
        (A) LENGTH: 24 base pairs
        (B) TYPE: nucleic acid -continued

```
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 22:

ATCGAGTTTT ACGTGGTTGT GGAC                                              24
```

HIGHLY PURIFIED MOCARHAGIN, A COBRA VENOM PROTEASE, POLYNUCLEOTIDES ENCODING SAME AND RELATED PROTEASES, AND THERAPEUTIC USES THEREOF

This application is a continuation of application Ser. No. 09/026,001, filed Feb. 18, 1998, now U.S. Pat. No. 6,413, 760, which is a continuation-in-part of application Ser. No. 09/012,637, filed Jan. 23, 1998, now abandoned, which was a continuation-in-part of application Ser. No. 08/843,373, filed Apr. 15, 1997, now abandoned.

BACKGROUND OF THE INVENTION

Cellular interactions are key to many events in vascular biology. Cell surface adhesion molecules mediate many of the interactions between leukocytes, platelets and the vessel wall. In response to inflammatory stimuli, leukocytes and platelets in the adjacent vasculature initially roll on the blood vessel wall, then stick, and finally transmigrate to the site of insult. The initial rolling event involves a class of adhesion proteins termed selectins (P-, E-, and L-selectin) which mediate the interaction between leukocytes, platelets and endothelial cells by their recognition of specific carbohydrate counter-structures, including sialyl-Lewis x. The primary sequence/motif structure of each of the selectins is similar. Each contains a N-terminal, 118-amino acid calcium-dependent lectin domain, an EGF motif, a variable number of tandem repetitive motifs related to motifs found in complement regulatory domains, a transmembrane domain and a short cytoplasmic tail.

P-selectin is a 140-kDa integral granule membrane glycoprotein localized to the $\alpha$-granules of platelets and the Weibel-Palade bodies of endothelial cells and is rapidly expressed on both cell types on cell activation. This suggests that endothelial P-selectin is a critical molecule mediating initial adhesion events in acute inflammation, a view recently supported by a number of in vivo inflammatory models including neutrophil-dependent acute lung injury (Mulligan et al. (1992) J. Clin. Invest. 90, 1600), endotoxin-induced neutropenia (Coughlan et al. (1994) J. Exp. Med. 179, 329), reperfusion injury (Asako et al. (1994) J. Clin. Invest. 93, 1508) and histamine-induced leukocyte rolling in post capillary venules (Weyrich et al. (1993) J. Clin. Invest. 91, 2620). P-selectin binds to 10,000–20,000 copies of a single class of binding sites on neutrophils and HL60 cells.

Sako et al. ((1993) Cell 75, 1179) have cloned a ligand for P-selectin, termed P-selectin glycoprotein ligand-1 (PSGL-1) found on the surface of leukocytes (see also copending application Ser. No. 08/316,305). PSGL-1 is a 220 kDa, disulfide-linked homodimeric sialomucin which, when expressed by recombinant methodology with the appropriate fucosyltransferase, binds P-selectin, E-selectin and L-selectin in a similar calcium-dependent manner to the PSGL-1 on neutrophils. PSGL-1 has a signal peptide sequence of 17 amino acids followed by a 24-amino acid PACE cleaved propeptide sequence. The mature N-terminus of PSGL-1 contains an unusual stretch of twenty amino acids which is rich in negatively-charged aspartate and glutamate residues and which contains three tyrosine residues which meet the consensus sequence for 0-sulfation by a golgi sulfotransferase. At least one of these tyrosine residues is sulfated as evaluated by site-directed mutagenesis (Sako et al.).

In addition to binding P-selectin, PSGL-1 also binds L- and E-selectin. In contrast to P-selectin, however, the requirements for E-selectin recognition are much less rigid. (Spertinit et al., J. Cell. Biol. 135:523 (1996)). E-selectin binds a wide variety of sialomucin structures if they co-express the sialyl-Lewis x structure. L-selectin binds to a number of different counter-receptors, GLYCAM-1, MadCAM-1 and CD34, which like PSGL-1, are also sialomucins. A major question currently unresolved is what determines selectin specificity in the recognition of specific counter-receptor structures. P-, E- and L-selectin are 60–70% homologous in their N-terminal, 118-amino acid lectin motifs and each similarly recognizes the sialyl-Lewis x and sialyl-Lewis a carbohydrate structures. Further, binding of P-selectin to its receptor on neutrophils is four to five orders of magnitude more avid than the binding of sialyl-Lewis x. While differences in specificity and avidity may in part be accounted for by either the presentation of multiple sialyl-Lewis carbohydrate structures on the receptor mucin core or by subtle differences in carbohydrate structure, it is probable that the protein component of the sialomucin also determines selectin interaction.

Although the inflammatory response mediated by the P-selectin/PSGL-1 interaction is a part of the body's normal defense system, inappropriate inflammatory responses can also result in the development of various inflammatory disease states. It would, therefore, be desirable to provide agents for interfering with or blocking the selectin/PSGL-1 interaction in order to treat inflammatory disease.

GPIb$\alpha$ is a component of the glycoprotein (GP) Ib-IX complex found on the surface of platelets and serving as a receptor for von Willibrand factor (vWF). The interaction of the GP Ib-IX complex with vWF mediates attachment of platelets to the blood vessel wall at the site of injury. It has also can cause aggregation of platelets in high shear conditions and enable platelet activation at low concentrations of thrombin.

Mocarhagin, a protease found in the venom of cobras (including the Mozambiquan spitting cobra, Naja mossambica mossambica, a.k.a. Naja mocambique mocambique), has been found to cleave PSGL-1, resulting in disruption of P- and L-selectin mediated cell adhesion. Preparations of mocarhagin have been reported and demonstrated to serve this purpose. See, U.S. Pat. No. 5,659,018; DeLuca et al., J. Biol. Chem. 270: 26734 (1995); Ward et al., Biochem. 35: 4929 (1996). (Spertini et al.)

In addition, it also has been reported that Mocarhagin is capable of cleaving GPIb$\alpha$ at a position proximal to sulfated tyrosine residues within the critical vWF binding domain and disrupting the binding activity of GPIb$\alpha$: DeLuca et al., J. Biol. Chem. 270: 26734 (1995); Dong et al., Biochemistry, 33: 13946 (1994).

It is therefore anticipated that an agent that can disrupt this interaction may have therapeutic application in a variety of thrombotic disorders such as restenosis and DVT.

However, applicants have discovered that the preparations described in these documents is only partially purified. Since it is necessary for mocarhagin proteins to be provided in highly purified form for such proteins to be used for therapeutic purposes, it would be desirable to provide highly purified preparations of mocarhagin proteins.

It would also be desirable to identify and isolate polynucleotides encoding mocarhagin proteins in order to produce such proteins by recombinant methods.

SUMMARY OF THE INVENTION

The present invention provides compositions comprising a mocarhagin protein at least 95% free of other cobra proteins (preferably 95% free of all other proteins). Preferably, the mocarhagin is homogeneous (i.e., free of other proteins). In preferred embodiments, the mocarhagin protein is full-length mocarhagin (as described below). In other embodiments, the mocarhagin protein is a fragment of full-length mocarhagin having mocarhagin proteolytic activity. Preferably, the mocarhagin protein is characterized by at least one characteristic selected from the group consisting of:

(a) a molecular weight of approximately 55 kDa under reducing conditions;

(b) a molecular weight of approximately 55 kDa under nonreducing conditions;

(c) an N-terminal amino acid sequence comprising TNTPEQDRYLQAKKYIEFYVVVDNVMYRKY (SEQ ID NO:1);

(d) mocarhagin proteolytic activity;

(e) the ability to inhibit platelet binding to vWF;

(f) requirement of calcium ion for activity;

(g) requirement of zinc ion for activity;

(h) an activity substantially inhibited by excess EDTA; and (i) an activity substantially inhibited by high concentrations of DFP.

In some embodiments, the mocarhagin protein has the N-terminal sequences TNTPEQDRYLQAKKYIEFYVVVDNVMYRKYTGKLHVITXXVYEMNALN (SEQ ID NO:2).

In particularly preferred embodiments, the mocarhagin protein is capable of cleaving capable of cleaving a material selected from the group consisting of anionic polypeptides containing sulfated tyrosine residues, PSGL-1 and GPIbα. PSGL-1 and/or GPIbα. Compositions comprising a therapeutically effective amount of a mocarhagin protein and a pharmaceutically acceptable carrier are also provided.

Methods of treating an inflammatory disease and thrombotic disorders and of inhibiting selectin-mediated binding comprising administering a therapeutically effective amount of a pharmaceutical composition comprising a mocarhagin protein to a mammalian subject are disclosed.

The invention also provides a method of isolating mocarhagin from venom, said method comprising:

(a) subjecting a composition comprising cobra venom to a heparin affinity chromatography column;

(b) subjecting the eluate from said heparin affinity column to a size exclusion column;

(c) subjecting the eluate from said size exclusion column to a Mono S column; and (d) eluting said mocarhagin from said Mono S column.

Compositions comprising a protein isolated according to these methods (and optionally further comprising a pharmaceutically acceptable carrier) are also encompassed by the claimed invention. Such compositions can also be used in methods of treating an inflammatory disease and of inhibiting selectin-mediated binding which comprise administering a therapeutically effective amount of such compositions to a mammalian subject.

The present invention also provides a composition comprising a mocarhagin protein, wherein said protein comprises an amino acid sequence selected from the group consisting of:

(a) the amino acid sequence of SEQ ID NO:6;

(b) the amino acid sequence of SEQ ID NO:6 from amino acid 24 to amino acid 621;

(c) the amino acid sequence of SEQ ID NO:6 from amino acid 192 to amino acid 621;

(d) fragments of the amino acid sequence of SEQ ID NO:6 encoding a protein having mocarhagin activity; and (e) the amino acid sequence encoded by the cDNA insert of clone NMM-1 deposited under accession number ATCC 209588;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:5;

(b) a polynucleotide comprising the nucleotide sequence of SEQ ID NO:5 from nucleotide 78 to nucleotide 1940;

(c) a polynucleotide comprising the nucleotide sequence of SEQ ID NO:5 from nucleotide 147 to nucleotide 1940;

(d) a polynucleotide comprising the nucleotide sequence of SEQ ID NO:5 from nucleotide 651 to nucleotide 1940;

(e) a polynucleotide encoding the mature protein encoded by the cDNA insert of clone NMM-1 deposited under accession number ATCC 209588;

(f) a polynucleotide encoding a protein comprising the amino acid sequence of SEQ ID NO:6;

(g) a polynucleotide encoding a protein comprising the amino acid sequence of SEQ ID NO:6 from amino acid 24 to amino acid 621;

(h) a polynucleotide encoding a protein comprising the amino acid sequence of SEQ ID NO:6 from amino acid 192 to amino acid 621;

(i) a polynucleotide encoding a protein comprising a fragment of the amino acid sequence of SEQ ID NO:6 encoding a protein having mocarhagin activity;

(j) a polynucleotide which is an allelic variant of a polynucleotide of (a)–(h) above;

(k) a polynucleotide which encodes a species homologue of the protein of (f), (g) or (h) above; and (l) a polynucleotide which hybridizes under stringent conditions to a polynucleotide of (a)–(h) above.

The present invention also provides a composition comprising a mocarhagin protein, wherein said protein comprises an amino acid sequence selected from the group consisting of:

(a) the amino acid sequence of SEQ ID NO:8;

(b) the amino acid sequence of SEQ ID NO:8 from amino acid 24 to amino acid 439;

(c) the amino acid sequence of SEQ ID NO:8 from amino acid 192 to amino acid 439;

(d) fragments of the amino acid sequence of SEQ ID NO:8 encoding a protein having mocarhagin activity; and (e) the amino acid sequence encoded by the cDNA insert of clone NMM-2 deposited under accession number ATCC 209589;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:7;

(b) a polynucleotide comprising the nucleotide sequence of SEQ ID NO:7 from nucleotide 85 to nucleotide 1401;

(c) a polynucleotide comprising the nucleotide sequence of SEQ ID NO:7 from nucleotide 154 to nucleotide 1401;

(d) a polynucleotide comprising the nucleotide sequence of SEQ ID NO:7 from nucleotide 658 to nucleotide 1401;

(e) a polynucleotide encoding the mature protein encoded by the cDNA insert of clone NMM-2 deposited under accession number ATCC 209589;

(f) a polynucleotide encoding a protein comprising the amino acid sequence of SEQ ID NO:8;

(g) a polynucleotide encoding a protein comprising the amino acid sequence of SEQ ID NO:8 from amino acid 24 to amino acid 439;

(h) a polynucleotide encoding a protein comprising the amino acid sequence of SEQ ID NO:8 from amino acid 192 to amino acid 439;

(i) a polynucleotide encoding a protein comprising a fragment of the amino acid sequence of SEQ ID NO:8 encoding a protein having mocarhagin activity;

(j) a polynucleotide which is an allelic variant of a polynucleotide of (a)–(h) above;

(k) a polynucleotide which encodes a species homologue of the protein of (f), (g) or (h) above; and (l) a polynucleotide which hybridizes under stringent conditions to a polynucleotide of (a)–(h) above.

The present invention also provides a composition comprising a mocarhagin protein, wherein said protein comprises an amino acid sequence selected from the group consisting of:

(a) the amino acid sequence of SEQ ID NO:10;

(b) the amino acid sequence of SEQ ID NO:10 from amino acid 24 to amino acid 613;

(c) the amino acid sequence of SEQ ID NO:10 from amino acid 192 to amino acid 613;

(d) fragments of the amino acid sequence of SEQ ID NO:10 encoding a protein having mocarhagin activity; and (e) the amino acid sequence encoded by the cDNA insert of clone NMM-9 deposited under accession number ATCC 209586;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:9;

(b) a polynucleotide comprising the nucleotide sequence of SEQ ID NO:9 from nucleotide 67 to nucleotide 1905;

(c) a polynucleotide comprising the nucleotide sequence of SEQ ID NO:9 from nucleotide 136 to nucleotide 1905;

(d) a polynucleotide comprising the nucleotide sequence of SEQ ID NO:9 from nucleotide 640 to nucleotide 1905;

(e) a polynucleotide encoding the mature protein encoded by the cDNA insert of clone NMM-9 deposited under accession number ATCC 209586;

(f) a polynucleotide encoding a protein comprising the amino acid sequence of SEQ ID NO:10;

(g) a polynucleotide encoding a protein comprising the amino acid sequence of SEQ ID NO:10 from amino acid 24 to amino acid 613;

(h) a polynucleotide encoding a protein comprising the amino acid sequence of SEQ ID NO:10 from amino acid 192 to amino acid 613;

(i) a polynucleotide encoding a protein comprising a fragment of the amino acid sequence of SEQ ID NO:10 encoding a protein having mocarhagin activity;

(j) a polynucleotide which is an allelic variant of a polynucleotide of (a)–(h) above;

(k) a polynucleotide which encodes a species homologue of the protein of (f), (g) or (h) above; and (l) a polynucleotide which hybridizes under stringent conditions to a polynucleotide of (a)–(h) above.

The present invention also provides a composition comprising a mocarhagin protein, wherein said protein comprises an amino acid sequence selected from the group consisting of:

(a) the amino acid sequence of SEQ ID NO:12;

(b) the amino acid sequence of SEQ ID NO:12 from amino acid 24 to amino acid 521;

(c) the amino acid sequence of SEQ ID NO:12 from amino acid 192 to amino acid 521;

(d) fragments of the amino acid sequence of SEQ ID NO:12 encoding a protein having mocarhagin activity; and (e) the amino acid sequence encoded by the cDNA insert of clone NMM-12 deposited under accession number ATCC 209585;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:11;

(b) a polynucleotide comprising the nucleotide sequence of SEQ ID NO:11 from nucleotide 78 to nucleotide 1640;

(c) a polynucleotide comprising the nucleotide sequence of SEQ ID NO:11 from nucleotide 147 to nucleotide 1640;

(d) a polynucleotide comprising the nucleotide sequence of SEQ ID NO:11 from nucleotide 651 to nucleotide 1640;

(e) a polynucleotide encoding the mature protein encoded by the cDNA insert of clone NMM-12 deposited under accession number ATCC 209585;

(f) a polynucleotide encoding a protein comprising the amino acid sequence of SEQ ID NO:12;

(g) a polynucleotide encoding a protein comprising the amino acid sequence of SEQ ID NO:12 from amino acid 24 to amino acid 521;

(h) a polynucleotide encoding a protein comprising the amino acid sequence of SEQ ID NO:12 from amino acid 192 to amino acid 521;

(i) a polynucleotide encoding a protein comprising a fragment of the amino acid sequence of SEQ ID NO:12 encoding a protein having mocarhagin activity;

(j) a polynucleotide which is an allelic variant of a polynucleotide of (a)–(h) above;

(k) a polynucleotide which encodes a species homologue of the protein of (f), (g) or (h) above; and (l) a polynucleotide which hybridizes under stringent conditions to a polynucleotide of (a)–(h) above.

The present invention also provides a composition comprising a mocarhagin protein, wherein said protein comprises an amino acid sequence selected from the group consisting of:

(a) the amino acid sequence of SEQ ID NO:14;

(b) the amino acid sequence of SEQ ID NO:14 from amino acid 24 to amino acid 592;

(c) the amino acid sequence of SEQ ID NO:14 from amino acid 192 to amino acid 592;

(d) fragments of the amino acid sequence of SEQ ID NO:12 encoding a protein having mocarhagin activity; and (e) the amino acid sequence encoded by the cDNA insert of clone NMM-13 deposited under accession number ATCC 209584;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:13;

(b) a polynucleotide comprising the nucleotide sequence of SEQ ID NO:13 from nucleotide 83 to nucleotide 1858;

(c) a polynucleotide comprising the nucleotide sequence of SEQ ID NO:13 from nucleotide 152 to nucleotide 1858;

(d) a polynucleotide comprising the nucleotide sequence of SEQ ID NO:13 from nucleotide 656 to nucleotide 1858;

(e) a polynucleotide encoding the mature protein encoded by the cDNA insert of clone NMM-13 deposited under accession number ATCC 209584;

(f) a polynucleotide encoding a protein comprising the amino acid sequence of SEQ ID NO:14;

(g) a polynucleotide encoding a protein comprising the amino acid sequence of SEQ ID NO:14 from amino acid 24 to amino acid 592;

(h) a polynucleotide encoding a protein comprising the amino acid sequence of SEQ ID NO:14 from amino acid 192 to amino acid 592;

(i) a polynucleotide encoding a protein comprising a fragment of the amino acid sequence of SEQ ID NO:14 encoding a protein having mocarhagin activity;

(j) a polynucleotide which is an allelic variant of a polynucleotide of (a)–(h) above;

(k) a polynucleotide which encodes a species homologue of the protein of (f), (g) or (h) above; and (l) a polynucleotide which hybridizes under stringent conditions to a polynucleotide of (a)–(h) above.

The present invention also provides a composition comprising a mocarhagin protein, wherein said protein comprises an amino acid sequence selected from the group consisting of:

(a) the amino acid sequence of SEQ ID NO:16;

(b) the amino acid sequence of SEQ ID NO:16 from amino acid 62 to amino acid 462;

(c) fragments of the amino acid sequence of SEQ ID NO:16 encoding a protein having mocarhagin activity; and (d) the amino acid sequence encoded by the cDNA insert of clone NMM-3 deposited under accession number ATCC 209587;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:15;

(b) a polynucleotide comprising the nucleotide sequence of SEQ ID NO:15 from nucleotide 3 to nucleotide 1388;

(c) a polynucleotide comprising the nucleotide sequence of SEQ ID NO:15 from nucleotide 186 to nucleotide 1388;

(d) a polynucleotide encoding the mature protein encoded by the cDNA insert of clone NMM-3 deposited under accession number ATCC 209587;

(e) a polynucleotide encoding a protein comprising the amino acid sequence of SEQ ID NO:16;

(f) a polynucleotide encoding a protein comprising the amino acid sequence of SEQ ID NO:16 from amino acid 62 to amino acid 462;

(g) a polynucleotide encoding a protein comprising a fragment of the amino acid sequence of SEQ ID NO:16 encoding a protein having mocarhagin activity;

(h) a polynucleotide which is an allelic variant of a polynucleotide of (a)–(g) above;

(i) a polynucleotide which encodes a species homologue of the protein of (e) or (f) above; and (j) a polynucleotide which hybridizes under stringent conditions to a polynucleotide of (a)–(g) above.

The present invention also provides a composition comprising a mocarhagin protein, wherein said protein comprises an amino acid sequence selected from the group consisting of:

(a) the amino acid sequence of SEQ ID NO:18;

(b) the amino acid sequence of SEQ ID NO:18 from amino acid 197 to amino acid 621;

(c) fragments of the amino acid sequence of SEQ ID NO:18 encoding a protein having mocarhagin activity; and (d) the amino acid sequence encoded by the cDNA insert of clone NMM-9ek deposited under accession number ATCC 209583;

the protein being substantially free from other mammalian proteins.

Yet other embodiments provide for a composition comprising an isolated polynucleotide selected from the group consisting of:

(a) a polynucleotide comprising the nucleotide sequence of SEQ ID NO:17;

(b) a polynucleotide comprising the nucleotide sequence of SEQ ID NO:17 from nucleotide 67 to nucleotide 1929;

(c) a polynucleotide comprising the nucleotide sequence of SEQ ID NO:17 from nucleotide 655 to nucleotide 1929;

(d) a polynucleotide encoding the mature protein encoded by the cDNA insert of clone NMM-9ek deposited under accession number ATCC 209583;

(e) a polynucleotide encoding a protein comprising the amino acid sequence of SEQ ID NO:18;

(f) a polynucleotide encoding a protein comprising the amino acid sequence of SEQ ID NO:18 from amino acid 197 to amino acid 621;

(g) a polynucleotide encoding a protein comprising a fragment of the amino acid sequence of SEQ ID NO:18 encoding a protein having mocarhagin activity;

(h) a polynucleotide which is an allelic variant of a polynucleotide of (a)–(g) above;

(i) a polynucleotide which encodes a species homologue of the protein of (e) or (f) above; and (j) a polynucleotide which hybridizes under stringent conditions to a polynucleotide of (a)–(g) above.

Compositions comprising an antibody which specifically reacts with the mocarhagin proteins or a fragments thereof having mocarhagin proteolytic activity are also provided.

DETAILED DESCRIPTION OF THE INVENTION AND PREFERRED EMBODIMENTS

Figure 1:
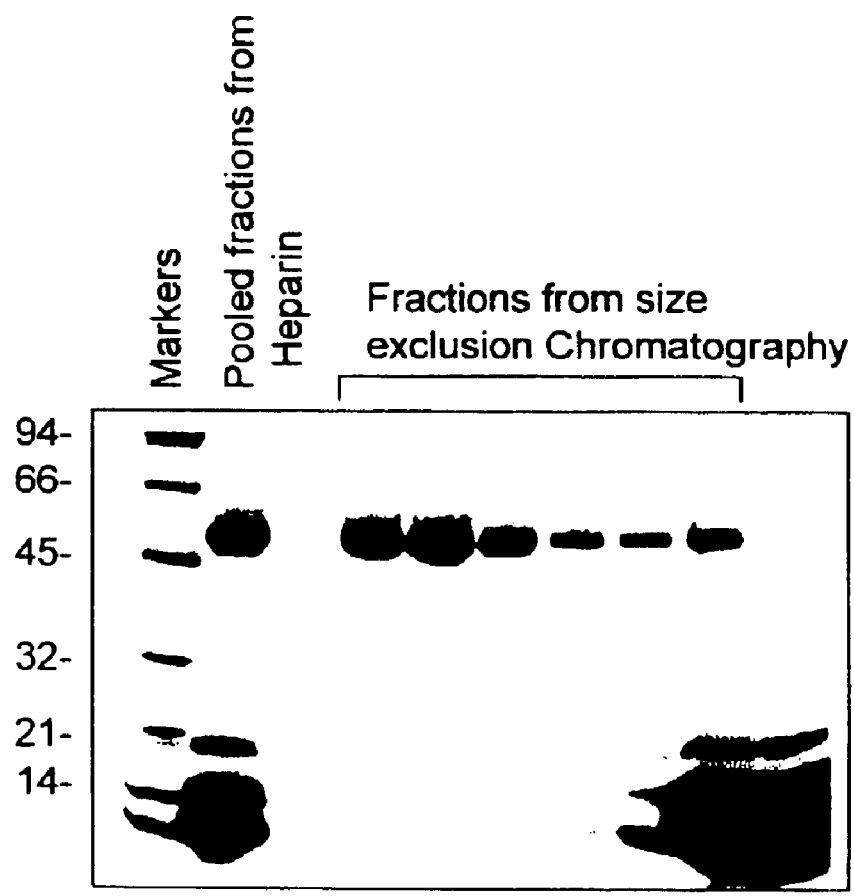
FIG. 1 depicts an SDS-PAGE gel analysis of fractions containing mocarhagin eluted from the size exclusion column as described herein. Multiple protein species of similar molecular weight can be seen in these fractions.

The present invention provides a highly specific metalloproteinase, mocarhagin, which has been purified from the venom of the Mozambiquan spitting cobra, Naja mossambica mossambica (a.k.a., Naja mocambique mocambique). Mocarhagin cleaves a ten amino acid peptide from the mature N-terminus of PSGL-1 and abolishes the ability of PSGL-1 to bind P-selectin. These results are in accord with the negative charge/sulfated tyrosine cluster at the N-terminus of PSGL-1 being an important determinant of P-selectin recognition in addition to the recognition of carbohydrate structure.

Mocarhagin can be purified from cobra venom according to the method described in the examples below. Other methods of purifying mocarhagin from cobra venom will also be apparent to those skilled in the art. The progress of any purification scheme for mocarhagin can be monitored on the basis of the biochemical characteristics of mocarhagin described herein and the assays for PSGL-1 digestion and neutrophil/HL60 cell binding described below.

A cDNA encoding a mocarhagin protein ("clone NMM-1") has also been cloned from a cobra venom gland library as described in Example 5 below. The nucleotide sequence of the NMM-1 cDNA is reported as SEQ ID NO:5. Clone NMM-1 was deposited with the American Type Culture Collection on Jan. 16, 1998 at accession number ATCC 209588. The protein sequence encoded by clone NMM-1 is reported as SEQ ID NO:6. Amino acids 1–23 of SEQ ID NO:6 are a predicted signal peptide. The mocarhagin propeptide begins with amino acid 24, with the mature protein beginning at amino acid 192.

Four additional full-length cDNAs encoding closely related proteases (clones "NMM-2", "NMM-9", "NMM-12" and "NMM-13") were also isolated from the cobra venom gland library as described in Example 5 below. Each of the proteins encoded by such cDNAs is also a "mocarhagin protein" as used herein.

The nucleotide sequence of the clone NMM-2 cDNA is reported as SEQ ID NO:7. Clone NMM-2 was deposited with the Americal Type Culture Collection on Jan. 16, 1998 at accession number ATCC 209589. The protein sequence encoded by clone NMM-2 is reported as SEQ ID NO:8. Amino acids 1–23 of SEQ ID NO:8 are a predicted signal peptide. The mocarhagin propeptide begins with amino acid 24, with the mature protein beginning at amino acid 192.

The nucleotide sequence of the clone NMM-9 cDNA is reported as SEQ ID NO:9. Clone NMM-9 was deposited with the Americal Type Culture Collection on Jan. 16, 1998 at accession number ATCC 209586. The protein sequence encoded by clone NMM-2 is reported as SEQ ID NO:10. Amino acids 1–23 of SEQ ID NO:10 are a predicted signal peptide. The mocarhagin propeptide begins with amino acid 24, with the mature protein beginning at amino acid 192.

The nucleotide sequence of the clone NMM-12 cDNA is reported as SEQ ID NO:11. Clone NMM-12 was deposited with the Americal Type Culture Collection on Jan. 16, 1998 at accession number ATCC 209585. The protein sequence encoded by clone NMM-12 is reported as SEQ ID NO:12. Amino acids 1–23 of SEQ ID NO:12 are a predicted signal peptide. The mocarhagin propeptide begins with amino acid 24, with the mature protein beginning at amino acid 192.

The nucleotide sequence of the clone NMM-13 cDNA is reported as SEQ ID NO:13. Clone NMM-13 was deposited with the Americal Type Culture Collection on Jan. 16, 1998 at accession number ATCC 209584. The protein sequence encoded by clone NMM-13 is reported as SEQ ID NO:14. Amino acids 1–23 of SEQ ID NO:14 are a predicted signal peptide. The mocarhagin propeptide begins with amino acid 24, with the mature protein beginning at amino acid 192.

Two additional partial cDNAs encoding other closely related proteases (clones "NMM-3" and "NMM-10") were also isolated from the cobra venom gland library as described in Example 5 below. Each of the proteins ecnoded by such cDNAs is also a "mocarhagin protein" as used herein.

The nucleotide sequence of the clone NMM-3 cDNA is reported as SEQ ID NO:15. Clone NMM-3 was deposited with the Americal Type Culture Collection on Jan. 16, 1998 at accession number ATCC 209587. The protein sequence encoded by clone NMM-3 is reported as SEQ ID NO:16. Amino acids 1–61 of SEQ ID NO:16 are part of the propeptide sequence. The mature mocarhagin protein begins with amino acid 62.

Applicants have also discovered that removal of the mocarhagin propeptide increases the catalytic activity of the enzyme. Thus engineered recombinant forms of mocarhagin include forms having endopeptidase cleavage sites between the propeptide segment and mature peptide segment, including but not limited to, enterokinase cleavage sites or PACE cleavage sites. Alternatively, a propeptide or secretory signal peptide may be substituted for the native mocarhagin propeptide to enable the secretion of active recombinant mocarhagin from eucaryotic host cells.

The NMM-9 cDNA was used to make a modified construct which includes an enterokinase cleavage sight. Certain preferred embodiments of the present invention included such an enterokinase cleavage site in order to increase production of active (i.e., properly cleaved to remove the leader sequence) protein. The nucleotide sequence of the construct containing the celavage site, clone NMM-9ek, is reported as SEQ ID NO:17. Clone NMM-9ek was deposited with the Americal Type Culture Collection on Jan. 16, 1998 at accession number ATCC 209583. The protein sequence encoded by clone NMM-9ek is reported as SEQ ID NO:18. The enterokinase cleavage site is found at amino acid 192–196 of SEQ ID NO:18. Amino acids 1–196 of SEQ ID NO:18 are part of the propeptide sequence which is cleaved upon enterokinase treatment. The mature cleaved mocarhagin propeptide begins with amino acid 197.

For the purposes of the present invention, a protein is defined as having "mocarhagin proteolytic activity" when (1) it digests PSGL-1, such as in the PSGL-1 digestion assay described in Example 3 below, and/or (2) inhibits the binding of P-selectin to neutrophils or HL60 cells, such as in the binding inhibition assay described in Example 2 below, and/or (3) cleaves a peptide derived from PSGL-1 (pyroEATEYEYLDYDFLPE, SEQ ID NO:3), such as in the peptide cleavage assay described in Example 4 below. Preferably, in the PSGL-1 digestion assay complete cleavage of $^{35}$[S]-sPSGL-1.T7 is achieved in 20 min. using 10 µg/mL mocarhagin protein; more preferably in 20 min. using less than 1 µg/mL mocarhagin protein. Preferably, in the neutrophil/HL 60 binding inhibition assay the mocarhagin protein exhibits an $IC_{50}$ of less than about 100 µg/mL, more preferably less than about 1 µg/mL.

Fragments of mocarhagin having mocarhagin proteolytic activity are also encompassed by the present invention. Fragments of mocarhagin having mocarhagin proteolytic activity can be identified by the PSGL-1 digestion assay and neutrophil/HL60 binding inhibition assay described below. Fragments of mocarhagin may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. For the purposes of the present invention, all references to "mocarhagin protein" herein include mocarhagin and fragments having mocarhagin proteolytic activity.

Isolated mocarhagin protein may be useful in treating conditions characterized by P- or E-selectin mediated intercellular adhesion or adhesion events mediated by GPIbα, including without limitation those involving platelet aggregation. Such conditions include, without limitation, myocardial infarction, vessel restenosis, thrombosis, bacterial or viral infection, metastatic conditions, inflammatory disorders such as arthritis, acute respiratory distress syndrome, asthma, emphysema, delayed type hypersensitivity reaction, systemic lupus erythematosus, thermal injury such as burns or frostbite, autoimmune thyroiditis, experimental allergic encephalomyelitis, multiple sclerosis, multiple organ injury syndrome secondary to trauma, diabetes, Reynaud's syndrome, neutrophilic dermatosis (Sweet's syndrome), inflammatory bowel disease, Grave's disease, glomerulonephritis, gingivitis, periodontitis, hemolytic uremic syndrome, ulcerative colitis, Crohn's disease, necrotizing enterocolitis, granulocyte transfusion associated syndrome, cytokine-induced toxicity, and the like. Mocarhagin protein may also be useful in organ transplantation, both to prepare organs for transplantation and to quell organ transplant rejection. Mocarhagin protein may be used to treat hemodialysis and leukophoresis patients. Mocarhagin protein may be used itself as an inhibitor of P- or E-selectin-mediated intercellular adhesion or to design inhibitors of P- or E-selectin-mediated intercellular adhesion. The present invention encompasses both pharmaceutical compositions containing mocarhagin protein and therapeutic methods of treatment or use which employ mocarhagin protein.

Mocarhagin protein may be used as a pharmaceutical composition when combined with a pharmaceutically acceptable carrier. Such a composition may contain, in addition to mocarhagin protein and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, G-CSF, Meg-CSF, stem cell factor, and erythropoietin. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with mocarhagin protein, or to minimize side effects caused by the mocarhagin protein. Conversely, mocarhagin protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which mocarhagin protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., healing of chronic conditions characterized by P-selectin- or E-selectin-mediated or GPIbα-mediated cellular adhesion or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of mocarhagin protein is administered to a mammal having a P-selectin-mediated or GPIbα-mediated disease state. Mocarhagin protein may be administered in accordance with the method of the invention either alone or in combination with other therapies such as treatments employing cytokines, lymphokines or other hematopoietic factors. When co-administered with one or more cytokines, lymphokines or other hematopoietic factors, isolated mocarhagin protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated mocarhagin protein in combination with cytokine(s), lymphokine(s), other hematopoietic factor(s), thrombolytic or anti-thrombotic factors.

Administration of mocarhagin protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of mocarhagin protein is administered orally, mocarhagin protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% mocarhagin protein, and preferably from about 25 to 90% mocarhagin protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of mocarhagin protein and preferably from about 1 to 50% mocarhagin protein.

When a therapeutically effective amount of mocarhagin protein is administered by intravenous, cutaneous or subcutaneous injection, mocarhagin protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to mocarhagin protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of mocarhagin protein in the pharmaceutical composition of the present invention will depend upon the nature and severity of the condition being treated, and on the nature of prior treatments which the patient has undergone. Ultimately, the attending physician will decide the amount of mocarhagin protein with which to treat each individual patient. Initially, the attending physician will administer low doses of mocarhagin protein and observe the patient's response. Larger doses of mocarhagin protein may be administered until the optimal therapeutic effect is obtained for the patient, and at that point the dosage is not increased further. It is contemplated that the various pharmaceutical compositions used to practice the method of the present invention should contain about 0.1 µg to about 100 mg of mocarhagin protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the mocarhagin protein will be in the range of 12 to 24 hours of continuous intravenous administration. Ultimately the attending physician will decide on the appropriate duration of intravenous therapy using the pharmaceutical composition of the present invention.

Mocarhagin protein of the invention may also be used to immunize animals to obtain polyclonal and monoclonal antibodies which specifically react with the mocarhagin protein and which may inhibit P-selectin-mediated or GPIbα-mediated cellular adhesion. Such antibodies may be obtained using the entire mocarhagin protein as an immunogen, or by using fragments of mocarhagin protein such as the soluble mature mocarhagin protein. Smaller fragments of the mocarhagin protein may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154(1963); J. L. Krstenansky, et al., FEBS Lett. 211, 10 (1987).

Also included in the invention are isolated DNAs which hybridize to the DNA sequence set forth in SEQ ID NO:5 under stringent (e.g. 4×SSC at 65° C. or 50% formamide and 4×SSC at 42° C.), or relaxed (4×SSC at 50° C. or 30–40% formamide at 42° C.) conditions.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the mocarhagin proteins recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the mocarhagin protein is expressed by a host cell which has been transformed (transfected) with the ligated polynucleotide/expression control sequence.

A number of types of cells may act as suitable host cells for expression of the mocarhagin protein. Suitable host cells are capable of attaching carbohydrate side chains characteristic of functional mocarhagin protein. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The mocarhagin protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the mocarhagin protein in lower eukaryotes such as yeast, fungi or in prokaryotes such as bacteria. Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli Bacillus subtilis, Salmonella typhimurium*, or any bacterial strain capable of expressing heterologous proteins. Suitable fungi strains include *Aspergillus* sp. or any fungi strain capable of expressing heterologous proteins.

The mocarhagin protein of the invention may also be expressed as a product of transgenic animals, e.g., as a component of the milk of transgenic cows, goats, pigs, or sheep which are characterized by somatic or germ cells containing a polynucleotide encoding the mocarhagin protein.

The mocarhagin protein of the invention may be prepared by culturing transformed host cells under culture conditions necessary to express a mocarhagin protein of the present invention. The resulting expressed protein may then be purified from culture medium or cell extracts as described in the examples below.

Alternatively, the mocarhagin protein of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the mocarhagin protein from culture supernatant may also include one or more column steps over such affinity resins as concanavalin A-agarose, heparintoyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the mocarhagin protein. Some or all of the foregoing purification steps, in various combinations, can also be employed to provide a substantially homogeneous isolated recombinant protein. The mocarhagin protein thus purified is substantially free of other mammalian or other host cell proteins and is defined in accordance with the present invention as "isolated mocarhagin protein".

EXAMPLES

The following examples are presented to illustrate, not to limit, the present invention.

Example 1

Purification of Mocarhagin 20 grams of crude protein from snake venom (Naja mossambica mossambica, Sigma, product no. V1627) were dissolved in 500 mL deionized $H_2O$ and centrifuged at 10 K rpm for thirty minutes at 4 C. The supernatant was loaded onto a 200 mL Heparin-650 M affinity column (Toyopearl, Tosohaas) equilibrated with 50 mm Tris-HCl ph 7.6 (buffer A) and 0.2M NaCl. The column was first washed extensively (to baseline) and mocarhagin was eluted with a gradient of 0.2–1.0 M NaCl in buffer A. Fractions containing the protease as monitored by SDS-PAGE (band with molecular weight ~55 kD) were pooled, concentrated using bentriprep-10 (Amicon) and applied to 21.5 mm ID×60 CM size exclusion column (G 3000SW, Tosohaas) in PBS at RT. Fractions eluted from the size exclusion column were analyzed by SDS-PAGE (FIG. 1), which showed the presence of multiple proteins of similar molecular weight.

Figure 2:
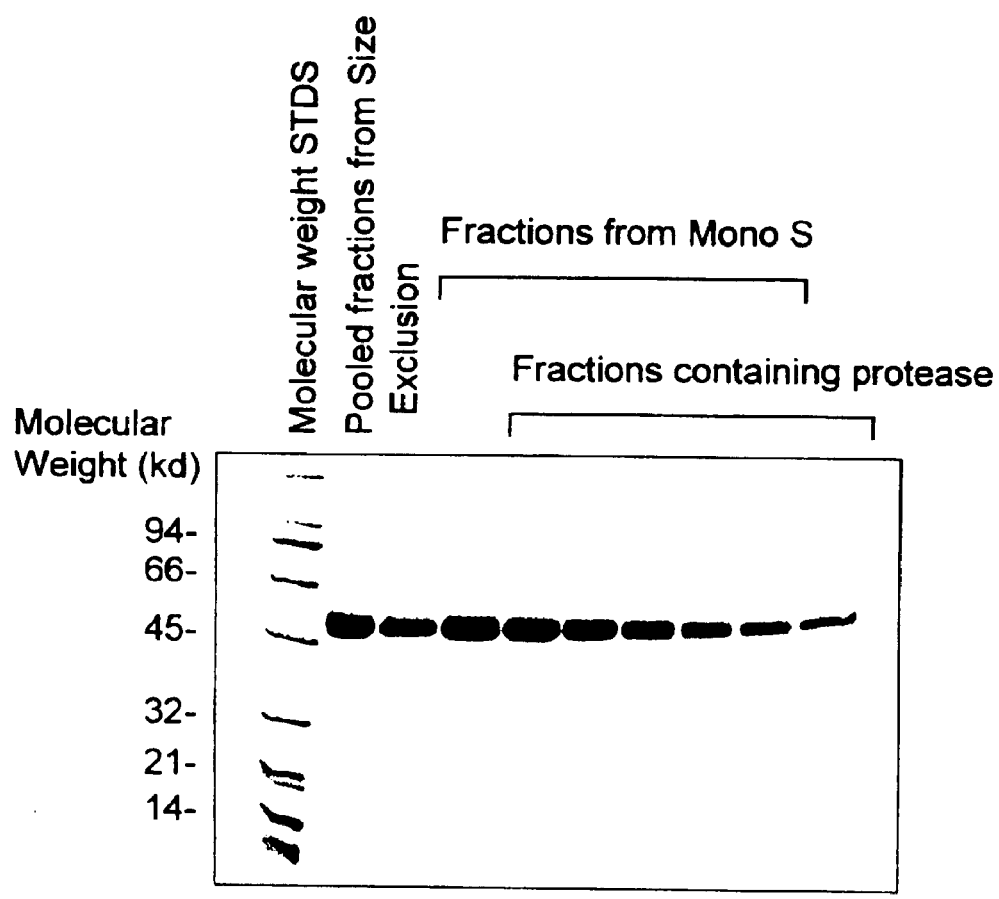
FIG. 2 depicts an SDS-PAGE gel analysis of fractions containing mocarhagin eluted from the Mono-S column as described herein. This gel demonstrates the high degree of purity of the mocarhagin material purified as described in Example 1.

Fractions containing mocarhagin were pooled and applied onto a Mono S 10/10 column (Pharmacia) equilibrated in 50 mm HEPES ph 8.0 (buffer B) at RT a O-IM NaCl in buffer B, gradient was used to elute the protein. The fractions were assayed by SDS-PAGE, pooled and frozen at 80 C. The recovery was 2–3 mg of mocarahagin per gram snake venom processed with a purity greater than 95%. FIG. 2 depicts a gel demonstrating the purity of the mocarhagin produced as herein described.

The N-terminal sequence was determined for the process described above as TNTPEQDRYLQAKKYIEFYVVVDN-VMYRKYTGKLHVITXXVYEMNALN (SEQ ID NO:2). The residues indicated in caps (TNTPEQDRYLQAKKYIEFYVVVDNVMYRKY, SEQ ID NO:1) were determined to a higher degree of certainty.

Example 2

Neutrophil/HL60 Binding Inhibition Assay

Neutrophils were isolated from venous blood anticoagulated with heparin (20 units/mL, final concentration) according to the method of Bignold and Ferrante ((1987) J. Immunol. Meth. 96, 29). The neutrophils were >95% pure as evaluated by flow cytometry and >98% viable by trypan blue exclusion. HL60 cells were cultured in RPMI medium supplemented with 10% fetal calf serum. Immediately before use, cells were washed twice with phosphate-buffered saline (0.01 M sodium phosphate, 0.15 M sodium chloride, pH 7.4). Neutrophils and cultured cells were finally resuspended at $2\times10^7$/mL in RPMI medium supplemented with 1% fetal calf serum. Binding of $^{125}$I-labeled P-selectin (Skinner et al.) to neutrophils or HL60 cells was evaluated by incubating $^{125}$I-labeled P-selectin (0.5 µg/mL, final concentration) with cells ($1\times10^7$/mL, final concentration) at 22° C. in a final volume of 200 µl. After 30 min, duplicate 50 µl aliquots were withdrawn and loaded onto 200 µl of 17% (w/v) sucrose in RPMI medium containing 1% fetal calf serum. Neutrophils were pelleted at 8,750×g for 2 min. After careful aspiration of the supernatant, radiolabel associated with the cell pellets was measured in a counter. Nonspecific binding of $^{125}$I-labeled P-selectin was assessed using a 50-fold excess of unlabeled P-selectin (Skinner et al.).

To examine the effect of pretreatment of neutrophils or HL60 cells with mocarhagin on P-selectin binding, washed cells ($2\times10^7$/mL) in RPMI made 1% in fetal calf serum were incubated in the presence or absence of 10 mM EDTA followed by mocarhagin (0.025–100 μg/mL, final concentrations) for 30 min at 22 C. P-selectin binding was then either directly assessed or was assessed after centrifugation of the cells, which were then washed twice and finally resuspended in RPMI with 1% fetal calf serum. In some experiments, DFP-treated mocarhagin was employed in place of mocarhagin. To evaluate the effect of supernatant from mocarhagin treated cells on P-selectin binding, HL60 cells at $10^8$/mL in 0.01 M Tris, 0.015 M sodium chloride, 0.001 M calcium chloride, pH 7.4, were incubated with mocarhagin (12 μg/mL) for 10 min at 22° C. The supernatant collected following centrifugation at 1000×g for 10 min was made 0.1% in BSA and loaded onto a heparin Sepharose CL-6B column (0.5×5 cm) to remove mocarhagin. The flow through was then tested for its effect on P-selectin binding to HL60 cells.

Example 3

PSGL-1 Digestion Assay

COS cells were cotransfected with three plasmids encoding soluble PSGL-1 (pED.sPSGL-1.T7; Sako et al.), alpha 1,3/1,4 fucosyltransferase (pEA.3/4FT) and soluble PACE (pEA-PACE SOL; Wasley et al. (1993) J. Biol. Chem. 268, 8458–8465). [$^{35}$S]Methionine-labeled COS conditioned medium containing sPSGL-1.T7 was digested with 5 μg/mL mocarhagin in TBS, 2 mM calcium chloride; 1 mg/mL BSA for 20 min at 37 C. The ability of sPSGL-1.T7 to bind P-selectin was assessed by precipitation with the P-selectin IgG chimera LECγ1 (Sako et al.) preabsorbed onto protein A Sepharose beads in TBS, 2 mM calcium chloride, 1 mg/ML BSA for 4 h at 4 C. A control experiment was also performed where the LECγ1 protein A Sepharose beads were pre-treated with mocarhagin and then exhaustively washed prior to presentation of sPSGL-1.T7. For immunoprecipitation analysis of untreated and mocarhagin treated sPSGL-1.T7, the protease was inactivated by the addition of 5 mM EDTA. sPSGL-1.T7 was then immunoprecipitated with anti-PSGL-1 polyclonal antibodies Rb3026 (raised against COS produced sPSGL-1.T7; Sako et al.) or Rb3443 (raised against the N-terminal peptide of PACE cleaved PSGL-1:QATEYEYLDYDFLPE, SEQ ID NO:4).

Example 4

Peptide Cleavage Assay

A digestion buffer (10 mM MOPS, 150 mM NaCl, 1 mM CaCl$_2$, 1 mM MgCl$_2$, 0.02% NaN$_3$, pH 7.5) and a peptide substrate solution (pyroEATEYEYLDYDFLPE (SEQ ID NO:3), 10 mM in DMSO) were prepared. 2.5 mL peptide substrate solution (250 μM final substrate concentration) was combined with mocarhagin sample material (10 μg/L final mocarhagin concentration) and adjusted to 100 μL with digestion buffer using no less than 75 μL. This mixture was digested at 37 C. for 16 hours in parallel with a control sample (no mocarhagin added).

50 μL aliquots of the digested samples were run on an RP-HPLC column (Vydac C18 218TP54, 4.6×250 mm), using the following solvents: solvent A, 0.1% TFA in H$_2$O; solvent B, 0.075% TFA in 90% AcN; flow rate 1 mL/min. The presence of peptides in the eluate was measured by absorbance at 214 nm, 260 nm and 280 nm. A positive assay result was indicated by observing elution of two peptide peaks in the tested sample which both elute earlier than the single peptide peak observed in the negative control.

Example 5

Cloning of Polynucleotide Encoding Mocarhagin Protein

Venom glands from five Mozambiquan spitting cobras, Naja mossambica mossambica, were dissected at two hour intervals, two to twelve hours following stimulation of venom production. Poly A+RNA was isolated from total RNA of the pooled gland tissue using an Oligotex Direct mRNA kit (Qiagen, Chatsworth, Calif.). Synthesis of cDNA was performed using Superscript Choice System (Gibco BRL, Gaithersberg, Md.) using oligo dT and random hexamer primers, EcoRI adapters. The cDNA was ligated with EcoRI digested lambda Zap II cloning vector (Stratagene, La Jolla, Calif.).

Using the above cDNA preparation as template, a PCR reaction was performed using degenerate oligonucleotides based on the N-terminal 30 residue amino acid sequence described above. The sequences of the forward primer consisted of 5'-ACNCCNGARCARGAY (SEQ ID NO:19). The sequences of the reverse primer consisted of 5'-RTAYTTYCKRTACAT (SEQ ID NO:20). A resulting 84 bp product was subsequently identified and DNA sequencing confirmed the sequence encoded 30 amino acid residues having a high degree of homology to the previously determined amino acid sequence. Two oligonucleotides 24 nucleotides in length, 5'-CAGGACAGGTACTTGCAGGCCAAA (SEQ ID NO:21) and 5'-ATCGAGTTTTACGTGGTTGTGGAC (SEQ ID NO:22), were synthesized based on the PCR product sequence and used as $^{32}$P hybridization probes to screen approximately $10^6$ plaques of plated lambda Zap II library. Duplicate sets of Duralose filters (Stratagene, La Jolla, Calif.) were hybridized seperately with each $^{32}$P hybridization probe in 5×SSC, 5× Denhardt's, 0.1% SDS, 50 ug/ml yeast tRNA 16 hrs @40 C. Filters were washed with 4× SSC, 0.1% SDS @ room temperature, then twice at 45 C. for 30 min. Autoradiography was −70 C. overnight with intensifying screen. Plaques showing positive hybridization to both probes were isolated and ultimately characterized by nucleotide sequencing.

Clones NMM-1, NMM-2, NMM-3, NMM-9, NMM-10, NMM-12 and NMM-13, described above, were isolated by this technique.

Example 6

Enterokinase Cleavage of NMM-9ek

COS cells were transfected with plasmid pED.NMM9ek, which included the cDNA sequence of SEQ ID NO:17 as an insert. This construct contains a novel enterokinase cleavage site between the propeptide and mature peptide of mocarhagin. After 48 hours, the transfected cells were washed in serum free medium, labelled with $^{35}$S methionine for 6 hours, and the serum free conditioned mediuma was harvested. Purified bovine enterokinase (La Vallie et al., 1993, J. BIOL. Chem. 268:23311–23317) was added at various concentrations to 100 ul conditioned medium with 10 mM Tris pH 8 and 1 mM CaCl$_2$, and incubate at 37 C. overnight. Soy Trypsin Inhibitor resin was added to remove the enterokinase from the reaction mixture. The resin was pelleted by centrifugation and the supernatant was then immunoprecipitated with rabbit polyclonal antibodies raised against mocarhagin purified from cobra venom.

Figure 3:
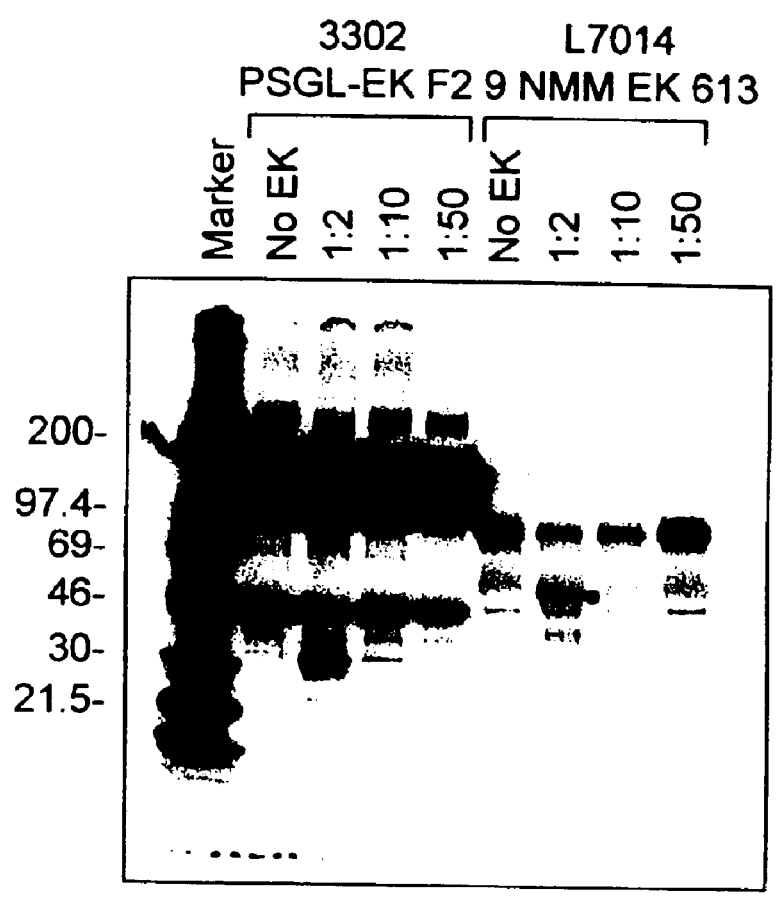
FIG. 3 is an SDS-PAGE gel analysis of fractions containing enterokinase-cleaved mocarhagin protein produced by expression of the NMM-9ek construct described below. The dot indicates the novel ~50 k band produced by enterokinase cleavage.

Following SDS-PAGE and autoradiography, a novel ~50 kD band appeared in the smple lane where 50 nanograms of purified bovine enterokinase had been incubated with the conditioned medium (see FIG. 3). This band is consistent with the expected molecular weight of the mature protease when the propeptide (~23 kD) is cleaved off.

What is claimed is:

1. A composition comprising a mature mocarhagin protein at least 95% free of other cobra proteins and comprising an N terminal amino acid sequence chosen from:
   a) amino acids 192 to 221 of SEQ ID NO: 6;
   b) amino acids 192 to 221 of SEQ ID NO: 8;
   c) amino acids 192 to 221 of SEQ ID NO: 10;
   d) amino acids 192 to 221 of SEQ ID NO: 12;
   e) amino acids 192 to 221 of SEQ ID NO: 14.

2. The composition of claim 1, wherein said mocarhagin protein exhibits an IC50 of less than about 100 µg/mL in a neutrophil/HL60 binding inhibition assay.

3. The composition of claim 1, wherein said mocarhagin protein is characterized by at least one characteristic selected from the group consisting of:
   (a) a molecular weight of approximately 55 kDa under reducing conditions;
   (b) a molecular weight of approximately 55 kDa under nonreducing conditions;
   (c) an N-terminal amino acid sequence comprising TNTPEQDRYLQAKKYIEFYVVVDNVMYRKY (SEQ ID NO: 1);
   (d) mocarhagin proteolytic activity;
   (e) the ability to inhibit platelet binding to vWF;
   (f) requirement of calcium ion for activity;
   (g) requirement of zinc ion for activity;
   (h) an activity substantially inhibited by excess EDTA; and
   (i) an activity substantially inhibited by high concentrations of DFP.

4. The composition of claim 1, wherein said mocarhagin protein is capable of cleaving a material selected from the group consisting of anionic polypeptides containing sulfated tyrosine residues, PSGL-1 and GP Ibα.

5. A composition comprising a therapeutically effective amount of a composition of claim 1, and a pharmaceutically acceptable carrier.

6. A composition comprising a mature mocarhagin protein isolated from cobra venom by:
   subjecting a composition comprising cobra venom to a heparin affinity chromatography column;
   (b) subjecting the eluate from said heparin affinity column to a size exclusion column;
   (c) subjecting the eluate from said size exclusion column to a Mono S column; and
   (d) eluting said mocarhagin from said Mono S column; and wherein and the mature mocarhagin protein comprises an N terminal amino acid sequence chosen from:
   a) amino acids 192 to 221 of SEQ ID NO: 6;
   b) amino acids 192 to 221 of SEQ ID NO: 8;
   c) amino acids 192 to 221 of SEQ ID NO: 10;
   d) amino acids 192 to 221 of SEQ ID NO: 12;
   e) amino acids 192 to 221 of SEQ ID NO: 14.

7. The composition of claim 6 further comprising a pharmaceutically acceptable carrier.

8. The composition of claim 2, wherein said mocarhagin protein exhibits an IC50 of less than about 1 µg/mL in a neutrophil/HL60 binding inhibition assay.

9. The composition of claim 1, wherein said mocarhagin protein is homogeneous.

10. The composition of claim 3, wherein said protein comprises the amino acid sequence of SEQ ID NO:6 from amino acid 192 to amino acid 621.

11. A composition comprising a mocarhagin protein, wherein said protein comprises an amino acid sequence selected from the group consisting of:
   (a) the amino acid sequence of SEQ ID NO:6;
   (b) the amino acid sequence of SEQ ID NO:6 from amino acid 24 to amino acid 621;
   (c) the amino acid sequence of SEQ ID NO:6 from amino acid 192 to amino acid 621;
   (d) fragments of the amino acid sequence of SEQ ID NO:6 encoding a protein having mocarhagin activity; and
   (e) the amino acid sequence encoded by the cDNA insert of clone NMM-1 deposited under accession number ATCC 209588; the protein being substantially free from other mammalian proteins.

12. The composition of claim 11, wherein said protein comprises the amino acid sequence of SEQ ID NO:6.

13. A protein produced according to a process comprising:
   (a) in a suitable culture medium, growing a culture of a host cell transformed with an isolated polynucleotide comprising the nucleotide sequence of SEQ ID NO:5 operably linked to an expression control sequence; and
   (b) purifying the protein from the culture.

14. The protein of claim 13 comprising a mature protein.

15. A pharmaceutical composition comprising a protein of claim 11 and a pharmaceutically acceptable carrier.

16. A composition comprising a mocarhagin protein, wherein said protein comprises an amino acid sequence selected from the group consisting of:
   (a) the amino acid sequence of SEQ ID NO:8;
   (b) the amino acid sequence of SEQ ID NO:8 from amino acid 24 to amino acid 439;
   (c) the amino acid sequence of SEQ ID NO:8 from amino acid 192 to amino acid 439;
   (d) fragments of the amino acid sequence of SEQ ID NO:8 encoding a protein having mocarhagin activity; and
   (e) the amino acid sequence encoded by the cDNA insert of clone NMM-2 deposited under accession number ATCC 209589; the protein being substantially free from other mammalian proteins.

17. The composition of claim 16, wherein said protein comprises the amino acid sequence of SEQ ID NO: 8.

18. A protein produced according to a process comprising:
   (a) in a suitable culture medium, growing a culture of a host cell transformed with an isolated polynucleotide comprising the nucleotide sequence of SEQ ID NO: 7 operably linked to an expression control sequence; and (b) purifying the protein from the culture.

19. The protein of claim 18 comprising a mature protein.

20. A pharmaceutical composition comprising a protein of claim 16 and a pharmaceutically acceptable carrier.

21. A composition comprising a mocarhagin protein, wherein said protein comprises an amino acid sequence selected from the group consisting of:

(a) the amino acid sequence of SEQ ID NO: 10;

(b) the amino acid sequence of SEQ ID NO: 10 from amino acid 24 to amino acid 613;

(c) the amino acid sequence of SEQ ID NO: 10 from amino acid 192 to amino acid 613;

(d) fragments of the amino acid sequence of SEQ ID NO: 10 encoding a protein having mocarhagin activity; and (e) the amino acid sequence encoded by the cDNA insert of clone NMM-9 deposited under accession number ATCC 209586; the protein being substantially free from other mammalian proteins.

22. The composition of claim 21, wherein said protein comprises the amino acid sequence of SEQ ID NO: 10.

23. A protein produced according to a process comprising:

(a) in a suitable culture medium, growing a culture of a host cell transformed with an isolated polynucleotide comprising the nucleotide sequence of SEQ ID NO: 9 operably linked to an expression control sequence; and (b) purifying the protein from the culture.

24. The protein of claim 23 comprising a mature protein.

25. A pharmaceutical composition comprising a protein of claim 21 and a pharmaceutically acceptable carrier.

26. A composition comprising a mocarhagin protein, wherein said protein comprises an amino acid sequence selected from the group consisting of:

(a) the amino acid sequence of SEQ ID NO: 12;

(b) the amino acid sequence of SEQ ID NO: 12 from amino acid 24 to amino acid 521;

(c) the amino acid sequence of SEQ ID NO: 12 from amino acid 192 to amino acid 521;

(d) fragments of the amino acid sequence of SEQ ID NO: 12 encoding a protein having mocarhagin activity; and (e) the amino acid sequence encoded by the cDNA insert of clone NMM-12 deposited under accession number ATCC 209585; the protein being substantially free from other mammalian proteins.

27. The composition of claim 26, wherein said protein comprises the amino acid sequence of SEQ ID NO: 12.

28. A protein produced according to a process comprising:

(a) in a suitable culture medium, growing a culture of a host cell transformed with an isolated polynucleotide comprising the nucleotide sequence of SEQ ID NO: 11 operably linked to an expression control sequence; and (b) purifying the protein from the culture.

29. The protein of claim 28 comprising a mature protein.

30. A pharmaceutical composition comprising a protein of claim 26 and a pharmaceutically acceptable carrier.

31. A composition comprising a mocarhagin protein, wherein said protein comprises an amino acid sequence selected from the group consisting of:

(a) the amino acid sequence of SEQ ID NO: 14;

(b) the amino acid sequence of SEQ ID NO: 14 from amino acid 24 to amino acid 592;

(c) the amino acid sequence of SEQ ID NO: 14 from amino acid 192 to amino acid 592;

(d) fragments of the amino acid sequence of SEQ ID NO: 14 encoding a protein having mocarhagin activity; and (e) the amino acid sequence encoded by the cDNA insert of clone NMM-13 deposited under accession number ATCC 209584; the protein being substantially free from other mammalian proteins.

32. The composition of claim 31 wherein said protein comprises the amino acid sequence of SEQ ID NO: 14.

33. A protein produced according to a process comprising:

(a) in a suitable culture medium, growing a culture of a host cell transformed with an isolated polynucleotide comprising the nucleotide sequence of SEQ ID NO: 13 operably linked to an expression control sequence; and (b) purifying the protein from the culture.

34. The protein of claim 33 comprising a mature protein.

35. A pharmaceutical composition comprising a protein of claim 31 and a pharmaceutically acceptable carrier.

36. A composition comprising a mocarhagin protein, wherein said protein comprises an amino acid sequence selected from the group consisting of:

(a) the amino acid sequence of SEQ ID NO: 16;

(b) the amino acid sequence of SEQ ID NO: 16 from amino acid 62 to amino acid 462;

(c) fragments of the amino acid sequence of SEQ ID NO: 16 encoding a protein having mocarhagin activity; and (d) the amino acid sequence encoded by the cDNA insert of clone NMM-3 deposited under accession number ATCC 209587; the protein being substantially free from other mammalian proteins.

37. The composition of claim 36, wherein said protein comprises the amino acid sequence of SEQ ID NO: 16.

38. A protein produced according to a process comprising:

(a) in a suitable culture medium, growing a culture of a host cell transformed with an isolated polynucleotide comprising the nucleotide sequence of SEQ ID NO: 15 operably linked to an expression control sequence; and (b) purifying the protein from the culture.

39. The protein of claim 38 comprising a mature protein.

40. A pharmaceutical composition comprising a protein of claim 36 and a pharmaceutically acceptable carrier.

41. A composition comprising a mocarhagin protein wherein said protein comprises an amino acid sequence selected from the group consisting of:

(a) the amino acid sequence of SEQ ID NO: 18;

(b) the amino acid sequence of SEQ ID NO: 18 from amino acid 197 to amino acid 621;

(c) fragments of the amino acid sequence of SEQ ID NO: 18 encoding a protein having mocarhagin activity; and (d) the amino acid sequence encoded by the cDNA insert of clone NMM-9ek deposited under accession number ATCC 209583; the protein being substantially free from other mammalian proteins.

42. The composition of claim 41, wherein said protein comprises the amino acid sequence of SEQ ID NO: 18.

43. A protein produced according to a process comprising:

(a) in a suitable culture medium, growing a culture of a host cell transformed with an isolated polynucleotide comprising the nucleotide sequence of SEQ ID NO:17 operably linked to an expression control sequence; and (b) purifying the protein from the culture.

44. The protein of claim 43 comprising a mature protein.

45. A pharmaceutical composition comprising a protein of claim 41 and a pharmaceutically acceptable carrier.

\* \* \* \* \*

UNITED STATES PATENT AND TRADEMARK OFFICE
CERTIFICATE OF CORRECTION

PATENT NO. : 6,881,404 B2
DATED : April 19, 2005
INVENTOR(S) : Amechand Boodhoo et al.

It is certified that error appears in the above-identified patent and that said Letters Patent is hereby corrected as shown below:

Column 59,
Line 49, after "claim 1", delete the comma.

Column 62,
Line 41, after "mocarhagin protein", insert a comma.

Signed and Sealed this

Sixteenth Day of August, 2005

JON W. DUDAS
*Director of the United States Patent and Trademark Office*